(12) United States Patent
Croy et al.

(10) Patent No.: US 7,094,561 B2
(45) Date of Patent: Aug. 22, 2006

(54) METHOD OF MONITORING THE MENSTRUAL CYCLE AND/OR PREGNANCY IN A FEMALE

(75) Inventors: Barbara Anne Croy, Niagara-on-the-Lake (CA); Sharon S. Evans, Hamburg, NY (US)

(73) Assignees: University of Guelph, Niagara-on-the-Lake (CN); Health Research, Inc., Roswell Park Division, Buffalo, NY (US)

(*) Notice: Subject to any disclaimer, the term of this patent is extended or adjusted under 35 U.S.C. 154(b) by 383 days.

(21) Appl. No.: 10/279,884

(22) Filed: Oct. 25, 2002

(65) Prior Publication Data

US 2003/0130592 A1 Jul. 10, 2003

Related U.S. Application Data

(63) Continuation-in-part of application No. PCT/CA01/01699, filed on Nov. 29, 2001.

(60) Provisional application No. 60/253,734, filed on Nov. 29, 2000.

(51) Int. Cl.
*G01N 33/53* (2006.01)

(52) U.S. Cl. .......................... 435/29; 435/7.1

(58) Field of Classification Search ............... 600/551; 514/21, 841; 530/399, 850; 424/139.1; 435/7.1, 7.2, 7.21
See application file for complete search history.

(56) References Cited

U.S. PATENT DOCUMENTS 4,208,479 A * 6/1980 Zuk et al. .................... 435/7.9
5,494,899 A * 2/1996 Kincade et al. ............... 514/21
6,805,863 B1 * 10/2004 Levy ....................... 424/139.1

FOREIGN PATENT DOCUMENTS

WO    WO 02/44716    * 6/2002

OTHER PUBLICATIONS

Croy B.A. et al., "Transplantation into Genetically Alymphoid Mice as an approach to Dissect the Roles of Uterine Natural Killer Cells during Pregnancy-A Review", Placenta, Mar. 2000, pp. 77-80, vol. 21, No. Sup. A.
Ashkar A.A. et al., "Functions of uterine natural killer cells are mediated by Interferon gamma production during murine pregnancy", Semin. Immunology, Aug. 2001, pp. 235-241, vol. 13, No. 4.
Chantarkru S. et al., "Contributions from self-renewal and trafficking to the uterine NK cell population of early pregnancy", Journal of Immunology, Jan. 1, 2002, pp. 22-28, vol. 168, No. 1.
King A. et al., "Human Uterine Natural Killer Cells", Natural Immunity, 1996-1997, pp. 41-52, vol. 15.
Croy B.A. et al., "A study on the density and distribution of uterine natural killer cells at mid pregnancy in mice", Journal of Reproductive Immunology, 2001, pp. 33-47, vol. 49.
Croy B.A. et al., "Histological studies of gene-ablated mice support important functional roles for natural killer cells in the uterus during pregnancy", Journal of Reproductive Immunology, 1997, pp. 111-133, vol. 35.
Moffett-King A., "Natural killer cells and pregnancy", Nat. Rev. Immunology, Sep. 2002, pp. 656-663, vol. 2, No. 9.
Gubbay O. et al., Prolactin induces ERK phosphorylation in epithelial and CD56(+) natural killer cells of the human endometrium, J. Clin. Endocrinol. Metab., May 2002, pp. 2329-2335, vol. 87, No. 5.
Emmer P.M. et al., "Altered phenotype of HLA-G expressing trophoblast and decidual natural killer cells in pathological pregnancies", Hum. Reprod., Apr. 2002, pp. 1072-1080, vol. 17, No. 4.
Ashkar A.A. et al., "Interferon gamma contributes to initiation of uterine vascular modification decidual integrity, and uterine natural killer cell maturation during normal murine pregnancy", J. Exp. Med., Jul. 17, 2000, pp. 259-270, vol. 192, No. 2.
Ashkar A.A. et al, "Interferon-gamma contributes to the normalcy of murine pregnancy", Biol. Reprod., Aug. 1999, pp. 493-502, vol. 61, No. 2.
Guimond M.J. et al., "Engraftment of bone marrow from severe combined immunodeficient (SCID) mice reverses the reproductive deficits in natural killer cell-deficient tg epsilon 26 mice", J. Exp. Med., Jan. 1998, pp. 217-223, vol. 187, No. 2.
Hunt J.S., et al, "Expression of the inducible nitric oxide synthase gene in mouse uterine leukocytes and potential relationships with uterine function during pregnancy", Biol. Reprod., Oct. 1997, pp. 827-836, vol. 57, No. 4.

* cited by examiner

Primary Examiner—Patrick J. Nolan
(74) Attorney, Agent, or Firm—Kramer & Amado, P.C.; Arlir M. Amado; Terry W. Kramer

(57) ABSTRACT

The present invention relates to methods of monitoring the menstrual cycle and/or the first half of pregnancy in a female by assessing the adhesion of lymphocytes from the female to uterine or lymphoid histological tissues from a pregnant animal or an animal that has been treated with gestational hormones. The method can be used to determine the ability of the lymphocyte donor's immune system to recognize and respond to an environment suitable for sustaining a pregnancy.

14 Claims, 13 Drawing Sheets

Pregnancy stimulates lymphocyte adhesion in uterine and peripheral lymph node tissues.

Adhesion in LN HEV of C57BL/6 Mice is Enhanced by Estrogen or Progesterone

Adhesion of fluorescently labelled spenocytes to LN

Effect of number of human lymphocytes applied to LN of pregnant mice on adhesion Effect of Anti-coagulent on Adhesion of Human Lymphocytes to LN of Pregnant Mouse \* Increased adhesion over EDTA and Na Citrate $p<0.05$ Effect of storage temperature on adhesion of human lymphocytes to Lymph nodes of pregnant mice

*Significantly different than freshly isolated control cells ($p<0.05$)

A

Effect of the Menstrual Cycle on Adhesion of Human PBL to LN of Pregnant Mice

B

Effect of the Menstrual Cycle on Adhesion of Human PBL to Pregnant Uterus of the Mouse

METHOD OF MONITORING THE MENSTRUAL CYCLE AND/OR PREGNANCY IN A FEMALE

RELATED APPLICATIONS

This application is a continuation-in-part of PCT/CA01/01699 filed Nov. 29, 2001 and claims priority from U.S. Provisional Patent Application No. 60/253,734 filed Nov. 29, 2000 and Canadian Patent Application No. 2,345,478, filed Apr. 27, 2001.

FIELD OF THE INVENTION

The present invention relates to methods of monitoring uterine status to determine the suitability for a successful pregnancy. More specifically, the present invention relates to methods of assessing or monitoring the menstrual cycle from the pre-ovulatory stage into the luteal phase and/or the first half of pregnancy by assessing the adhesion of human lymphocytes to uterine or lymphoid tissues under the influence of gestational hormones.

BACKGROUND OF THE INVENTION

Transient granulated lymphocytes are described in the pregnant uteri of >20 species[1]. In women and mice, these cells are Natural Killer (NK) cells and their activation/maturation depends upon uterine decidualization rather than presence of conceptuses.[2,3] The life history and functions of uterine NK (uNK) cells are more fully known in rodents than women. In women, uNK cells are most frequent in first trimester, representing over 70% of the nucleated bone marrow-derived cells in decidual cell suspensions. Human data also suggest that uNK cells are distinctive, tissue based cells. Most circulating human NK cells are $CD16^+$ $CD56^{dim}$; uNK cells are $CD16^-$ $CD56^{bright}$ [2,4]. The minor circulating $CD56^{bright}$ subset preferentially expresses (95%) very high levels of L-selectin[5], a molecule central to initiation of extravasation. Fewer $CD56^{dim}$ circulating cells (24%) express L-selection and at a much lower surface density[5]. The two major NK cells functions, target cell lysis and cytokine production, may be displayed separately or dually by single cells[6]. Human uNK cells display both functions in vitro[7-9] but their in vivo functions are undefined. Many current studies of human uNK function address interactions with trophoblast[10-12]. Other recent reports indicate human uNK cells express angiogenic factors including Ang-2[13], an antagonist to endothelial cell TIE-2 and thus, a vessel destabilizing molecule and NKG5, a potent endothelial cell mitogen[14].

In vivo studies of murine uNK cell functions advanced rapidly after availability of strains genetically deficient in NK cells[15,16]. Histological studies established that NK cell deficient mice do not differentiate uNK cells[17,18]. In NK-deficient strains with unrelated genetic changes, a common uterine phenotype was developed by 48 hr after implantation. The anomalies were endothelial cell hypertrophy and damage in mesometrially-positioned uterine vessels, lack of uterine arteriole wall and lumen changes indicative of pregnancy and hypocellularity of decidua. Absence of lytic NK cell function does not explain these results, thus, a cytokine deficiency hypothesis was pursued. Interferon-gamma (IFN-γ) is the prototypic cytokine product of NK cells. IFN-γ is an induced molecule known to regulate expression of >1000 genes, many of which are expressed by vascular and decidual tissues[19,20]. IFN-γ is expressed in human and murine uteri during normal gestation[21-23] but many authors regard IFN-γ as detrimental to pregnancy[24,25]. In an experimental series, it was found (i) IFN-γ peaks in mouse mesometrial uterus at gestation day (gd) 10 at 10 IU/implantation site and (ii) only 10% of this comes from non uNK cells[26]. Transplantation showed that higher levels of uNK-cell derived IFN-γ are essential for pregnancy-induced modification of the spiral arteries and integrity of decidua while the lower level, non lymphocyte-derived IFN-γ is adequate for maturing uNK cells and limiting their numbers. Daily recombinant muIFN-γ (100–1000 IU/6 days) in alymphoid mice promoted full uterine artery modification and normalized deciduas[27]. Tumor necrosis factor-alpha, another NK and uNK cell product, lacked these effects[26,27].

Mechanisms that transform endometrium to decidua are endocrine-related. In humans, decidualization begins 7–14 days after the surge in luteinizing hormone (LH) (LH+7–14) and continues if pregnancy occurs[28-30]. Early decidual development appears important for implantation and most human pregnancy wastage occurs in this peri-implantation interval. Human uNK cells begin to increase in number about LH+3, encircling arteries and uterine glands. Stromal cell changes that cuff the spiral arteries (Streeter's columns) are seen at LH+8. By LH+11 to +13, very large numbers of uNK cells are found throughout the stroma accounting for 30–40% of all cells[4]. Gap junction-like contacts are found between some human uNK cells and early decidua, that appear essential to the continued differentiation of both cell types[31], suggesting that normal uNK cell numbers and levels of function contribute to human implantation success.

Reproductive cycles of mice differ to human by virtual absence of a luteal phase. Decidualization and uNK cell activation are initiated by implantation, thus, uNK cell deficits do not influence mouse embryo implantation[17,22]. UNK cells proliferate rapidly within decidua[2,3] but recently it was established that self-renewing uNK progenitor cells do not reside there. Uterine segments from normal mice were grafted by end-to-end anastomosis into uNK cell deficient or normal recipients who were then mated. uNK cells were generated only when hosts had NK cell progenitors[33,34]. In pregnant mammals, thymus and marrow involute during pregnancy[35,36] while spleen and lymph nodes (LN) become hypercellular[37,38]. By transplanting to NK cell deficient mice with established pregnancies, it was found that gestation induces acute uNK cell recruitment from spleen but not from marrow or thymus. uNK cells appear to be recruited to decidua basalis and then move into the mesometrial triangle, the entry portal for nerves and vessels supplying the uterus and developing feto-placenta units[3,39,40]. In decidua basalis of normal mice at mid gestation, 7% of uNK cells are within vessels homologous to spiral arteries, another 30% are in walls of these vessels and the remaining cells, as resolved in paraffin-embedded sections, are associated with other tissues[41].

In normal mice, uNK cells are a major source of inducible nitric oxide synthase[22], an IFN-γ regulated enzyme producing the powerful vasodilator nitric oxide (NO). In uNK cell deficient mice, expression of this enzyme is induced in trophoblast but at very low levels[22] that cannot dilate the spiral arteries (Kiso and Croy, unpublished vascular casting data). Ineffective dilation of spiral arteries is a hallmark of the human gestational complication hypertension/pre-eclampsia[42,43]. Despite extensive study of this syndrome, its frequency remains constant and there is no consensus on underlying causes[44,45]. Systemic endothelial cell damage underlies clinical symptoms and may be mediated by dysregulated blood cytokine balance[46,47]. Some authors suggest immunological contributions[48-50] but assessment of changes in frequency or functional activities of uNK cells is just beginning[51-53]. Women achieving pregnancy by assisted reproductive technology (ART) are reported at higher risks for pre-eclampsia than women carrying naturally conceived conceptuses[54-60]. Thus, inappropriate uterine recruitment of human NK cells may contribute to two health-related problems: implantation failure through lack of decidual maintenance and predisposition in pregnant women to preeclampsia. Therefore, it is critically important to define the molecules contributing to the movement of human uNK cells and their progenitors into the uterus and to the specification of their intrauterine locations. Subnormal uNK cell frequencies are reported in women with recurrent spontaneous abortion[61], suggesting an additional obstetrical group that may benefit from the proposed studies.

Movement of leukocytes from vessels into tissue has been extensively characterized in non-reproductive organs and many techniques have been validated for such work[62-65]. Lymphocytes constitutively express the tethering molecule L-selectin, which interacts with Peripheral LN Addressin (PNAd) and Mucosal Vascular Addressin-1 (MAdCAM-1) expressed by the microvillous surface of endothelium in LN and Peyers Patches (PP). Avidity of these interactions is modulated by physiological responses including cytokines, inflammation and fever which trigger rolling for egress of non activated lymphocytes from vessels[5, 66-68]. Firmer adhesion and trans-endothelial migration involve integrins, particularly $\alpha 4\beta 7$, which uses MAdCAM-1. Recruitment of activated cells requires only the latter mechanism and down regulation of L-selectin is paired with upregulation of $\alpha 4\beta 7$ as naive cells begin to roll and dock. In the presence of cytokines, Vascular Cell Adhesion Molecule 1 (VCAM-1) is induced on endothelium and utilized by lymphocytes[69]. The $\beta 2$ integrin, Leukocyte Function Associated Antigen-1, (LFA-1) interacting with its ligands Intercellular Adhesion Molecules (ICAM)-1 and -2 also mediates firm adhesion but is not modified by fever ranges similar to those seen at human ovulation[68].

In view of the foregoing, there is a need in the art to define the molecules contributing to the movement of human uterine NK cells and their progenitors into the uterus in order to determine if the uterine environment is amenable to sustaining a pregnancy.

SUMMARY OF THE INVENTION

Uterine natural killer (NK) cells are required to maintain the integrity of the decidualized uterine stroma and for initiating decidual artery instability. Failure to recruit adequate uterine NK cells to the human uterus may lead to a collapsing decidua that would limit implantation success or contribute to gestational hypertension with or without pre-eclampsia.

The inventors have determined that uterine NK cells do not self-renew in the uterus but rather are recruited to the uterus from the periphery. It is expected that cyclic endocrine changes in the late menstrual cycle and early pregnancy in women, open molecular gates in uterine endothelium that promote movement of NK cells and their precursors into the uterus. Further, the inventors submit that defects in appropriate NK cell trafficking compromise establishment of pregnancy and/or lead to patients being classified as infertile or pre-eclamptic.

The inventors have also shown that human lymphocytes show increased adhesion to uterine or lymphoid tissue from a pregnant or gestational-hormone-treated mouse compared to uterine or lymphoid tissue from a non-pregnant, non-gestational-hormone-treated mouse or other non-lymphoid or non-uterine tissue. This adhesion of lymphocytes was found to peak on the day of luteinizing hormone (LH) surge, which occurs about mid-way through the menstrual cycle, in the peri-ovulatory period.

Accordingly, the present invention provides a method of monitoring a menstrual cycle and/or pregnancy in a female comprising detecting the adhesion of lymphocytes from the female with uterine or lymphoid tissue from a pregnant animal or an animal that has been treated with gestational hormones, such as luteinizing hormone, chorionic gonadotropin, estrogen and/or progesterone. The invention also includes the identification of lymphocyte subsets involved in the adhesion and to determining the effect of pituitary and ovarian hormones on the interactions between lymphocytes and uterine or lymphoid endothelium. The invention further relates to the determination of the effect of controlled ovarian hyperstimulation (COH) with fertility drugs on the interaction between the lymphocytes and the uterine or lymphoid endothelium.

The present invention further relates to kits for performing the method of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

* indicates a significantly different mean (p<0.05) to that in the same tissue from virgin females (v) as analyzed by ANOVA (SAS 6.12, SAS Institute, Cary, N.C.). Each function-blocking mAb treatment lowered adhesion compared to that seen in untreated samples (p<0.001 using Student's t test).

Figure 3:
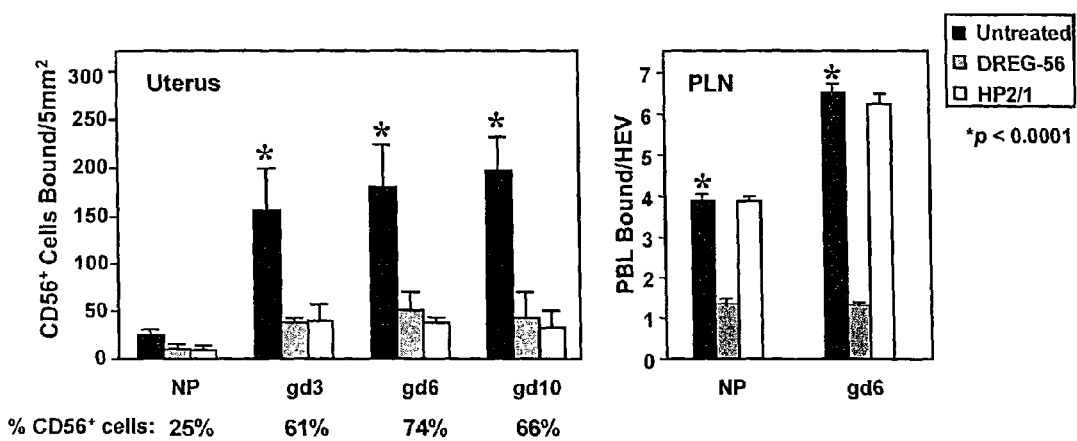

FIG. 3 shows histograms illustrating the influences of 17-beta estradiol and/or progesterone treatment of ovariectomized B6 mice on adhesiveness of high endothelial venules (HEV) of peripheral lymph nodes (PLN; A and C), Peyer's Patches (PP; B and D) and Pancreas (E and F). Assays were conducted using human PBL indicator cells with PLN and mouse TK-1 lymphoma cells with PP. Cryostat sections were prepared from tissues collected from mice treated with 17-β estradiol at 100 ng/day (E2low), 1 μg/day (E2high), progesterone (1 mg/day, P4), combined steroids (E2/P4), and combined steroids plus induction of deciduoma (E2/P4+deciduoma). Tissues from virgin and Ovx B6 mice were used for controls. Data are the mean±SD and are representative of the data from multiple experiments for Panels A and B (n=3) and for 2 mice per group in Panels C, D, E and F.

+=significantly different to the virgin or oil placebo treatment groups (p<0.05)

*=significantly different level of adhesion to the same tissue compared with untreated cells (p<0.001)

Figure 4:
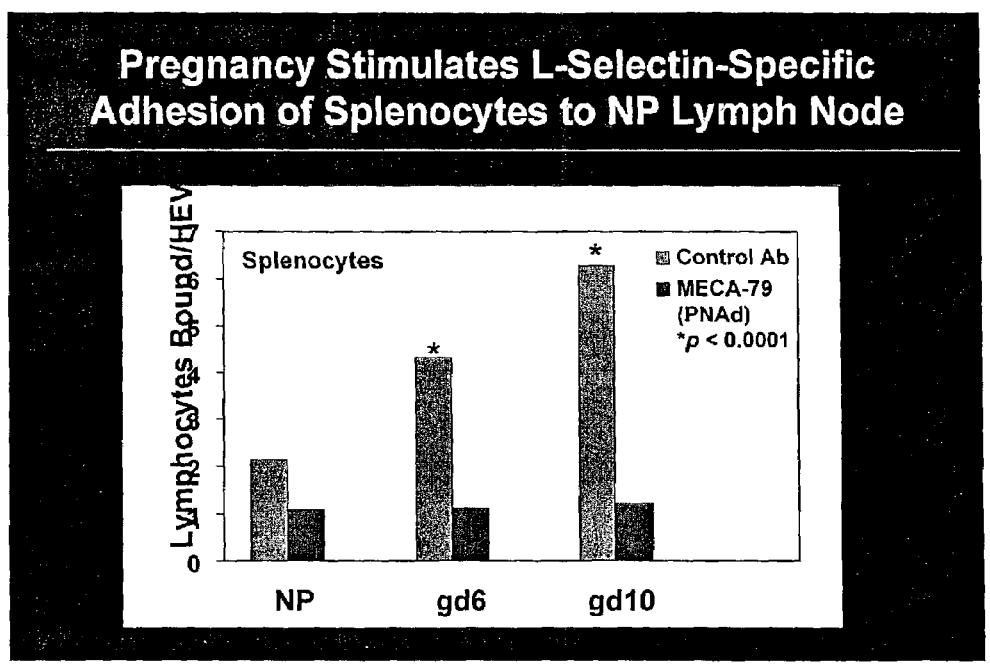

FIG. 4 shows histograms illustrating the influences of 17-beta estradiol and/or progesterone treatment of ovariectomized B6 mice on adhesiveness of uterine tissue for $CD56^{bright}$ human lymphocytes. Assays were conducted using human PBL pre-labeled with anti-CD56 mAb (NKG1, Coulter Immunology, diluted 1:100) followed by rabbit anti-mouse Ig-rhodamine isothiocynate (RITC) Ab as indicator cells and were scored by fluorescence microscopic examination. Cryostat sections were prepared from tissues collected from mice treated with 17-β estradiol at 100 ng/day (E2low), 1 μg/day (E2high), progesterone (1 mg/day, P4), combined steroids (E2/P4), and combined steroids plus induction of deciduoma (E2/P4+deciduoma). Uteri from virgin and Ovx B6 mice were used for controls. The histograms show means±SD and are representative of the data from at least 3 mice per group.

+=significantly different to the virgin and oil placebo treatment groups (p<0.05)

*=significantly different level of adhesion to the same tissue compared with cells not treated with a function-blocking mAb (p<0.001)

Figure 5:
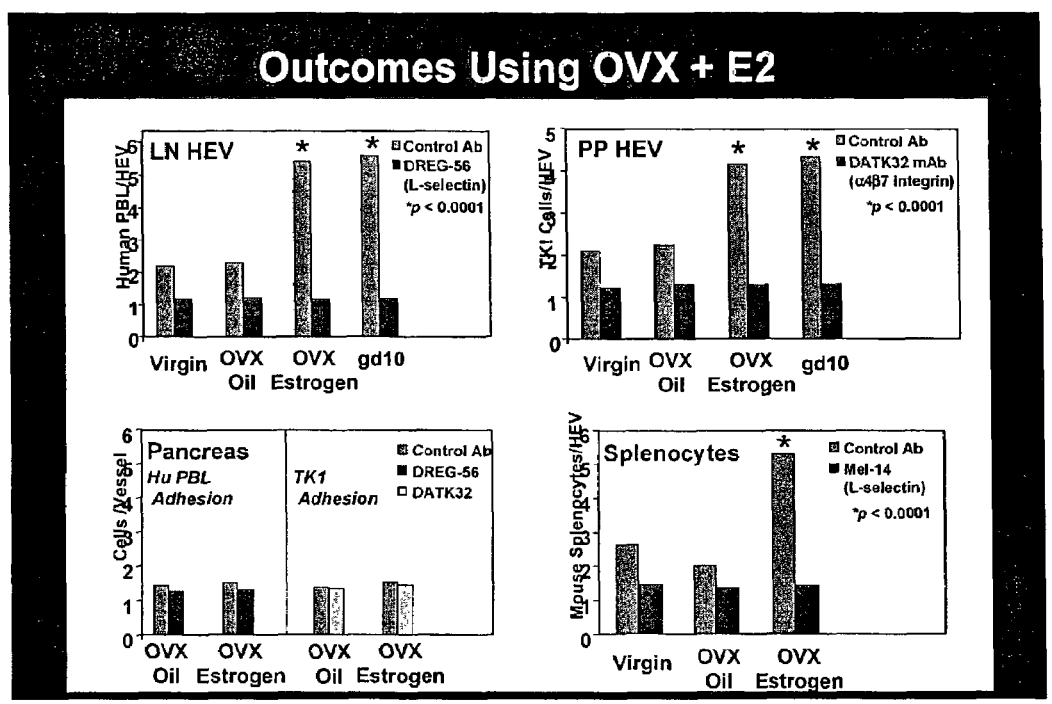

FIG. 5 shows histograms comparing uterine adhesiveness at gestation day (gd) 6 to that of uteri from ovariectomized mice treated with placebo (oil) or with therapeutic levels of 17-beta estradiol (E2high) for $CD56^{bright}$ human lymphocytes (means±SD for 10 high power fields; HPF). $CD56^{bright}$ cells were <2% of the starting population as analyzed by flow cytometry (not shown). The % enrichment in this subset, recognized as $CD56^{bright}$ by microscopy, through binding to uterine tissue is indicated numerically below each treatment group.

*=significantly reduced adhesion of $CD56^+$ cells (p<0.001) treated with antibodies DREG-56 (L-selectin) or HP2/1 ($α_4$ integrin) as compared to untreated groups.

Figure 6:
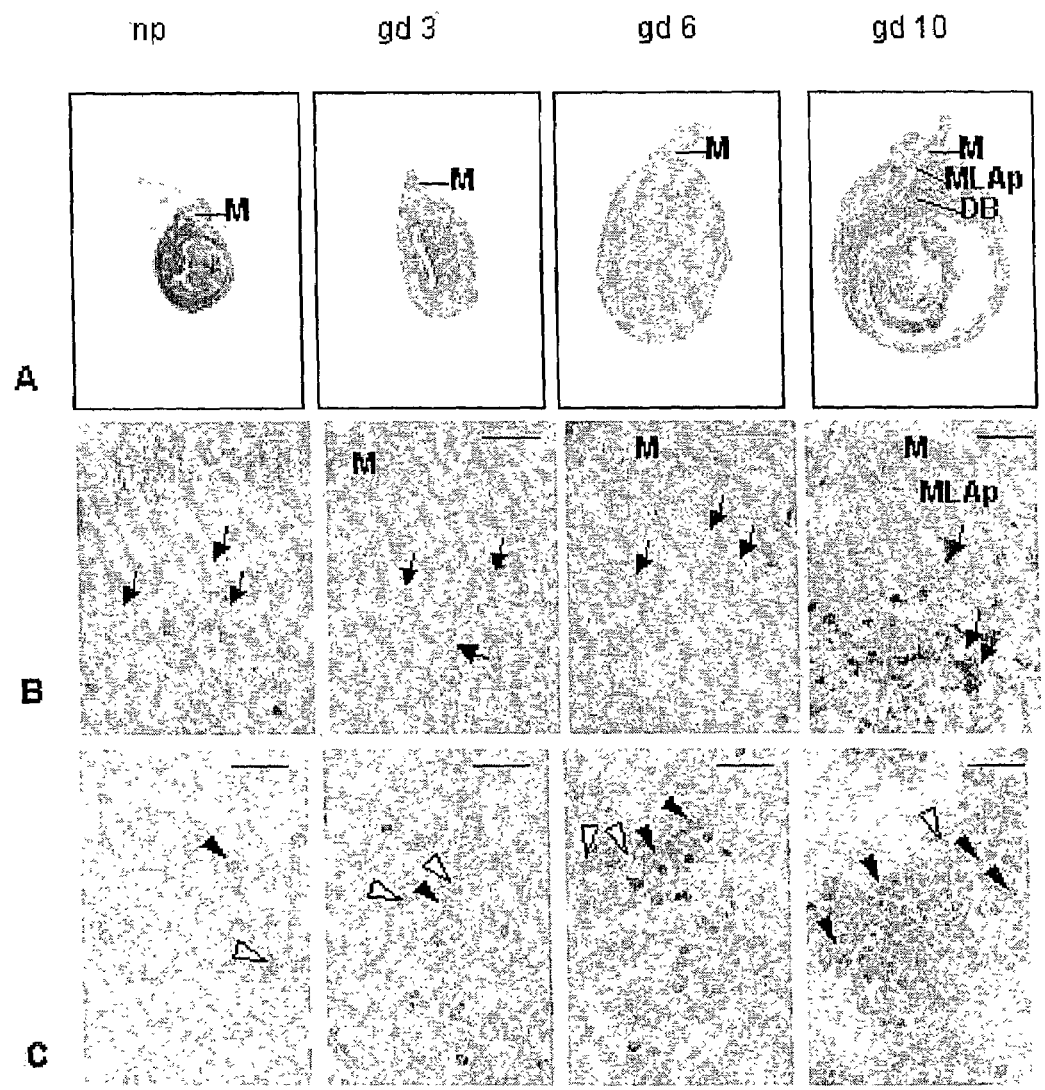

FIG. 6 shows histological images of uterine tissue. Row A depicts low power histological images of uterus and implantation sites in B6 mice stained with H & E, to provide orientation. The mesometrial triangle (M), where development of the mesometrial lymphoid aggregate of pregnancy (MLAP) occurs, is uppermost in all panels. The antimesometrial (AM) side of the uterus is at the bottom of all images. At gestation day (gd) 3, decidualization has yet to commence. At gd 6, maternal decidual tissue (D) fills the uterus, with the embryo at the primitive streak stage occupying the embryonic crypt (EC). By gd 10, there is a fully developed implantation site. The microdomains of the MLAp and decidua basalis (DB) are maternal in origin while that of the placental trophoblast (P) is fetally-derived. Anti-mesometrial decidua has regressed as the fetus (F) has developed and grown. Rows B and C show low and high power images, respectively, of toluidine blue stained human lymphocytes (some marked by arrows) adhering to thick cryostat sections of mouse uterus at the stages indicated above the images. Binding to decidualized uteri occurred only in the DB. Lymphocyte clustering was prominent at gd 10. Lymphocytes binding to non-decidualized uteri were dispersed as single cells (70% small, 30% large) with random distribution in the virgin uterus. The most frequently bound cells at gd 3 were dispersed, typical small lymphocytes (85%, black arrowheads) while 15% of bound cells were larger (white arrowheads). As gestation progressed to gd 6, adhesion became restricted to DB, the proportion of large cells declined to 1%, numbers of adherent cells increased and some appeared as stable clusters of up to 30 cells. The clusters were much larger at gd 10 than at gd 6, but the proportion of large adhered cells declined (3%). Row B Bar=150 μm, Row C Bar=40 μm.

Figure 7:
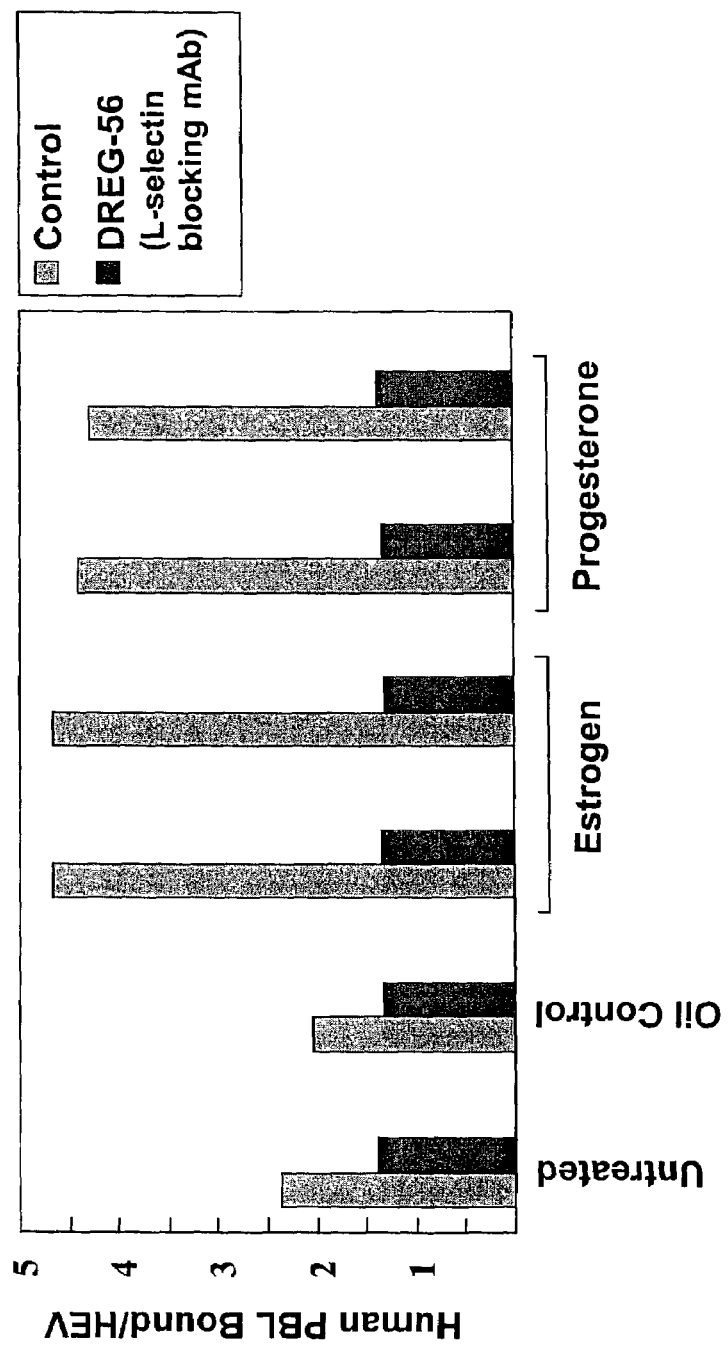

FIG. 7 shows histograms illustrating the adhesiveness of splenocytes for HEV in PLN is altered by ovarian steroid hormones (Panel A) and by pregnancy to levels seen in fever range hyperthermia (Panel B). Splenic lymphocytes were collected from ovariectomized mice receiving the treatments outlined in FIG. 1, from pregnant mice or from virgin mice and tested for adhesion to PLN from virgin mice. Some of the splenocytes from virgin mice were incubated at 37° C. while others were incubated at 40° C., prior to use in the adhesion assay. In Panel A, bars represent the mean±SD for bound lymphocytes from a normal virgin B6 mouse and for the ovariectomized mice in each treatment group.

Open bars represent the mean numbers of adhering lymphocytes after treatment with the mAb MEL-14 which blocks the function of mouse L-selectin. All blocking was statistically significant (p<0.001) using Student's t-test. Panel B presents the comparisons between the gains in adhesion induced by mild temperature elevation in splenocytes from virgin mice and the peak gains induced by pregnancy (gd 8 and gd 9). The three test groups were each statistically different to the virgin group (p<0.05) but did not differ from each other. Blocking with MEL-14 significantly reduced adhesion (p<0.001,) when pairs of untreated and treated lymphocytes were compared.

+=significantly different between groups (p<0.05 by ANOVA)

*=significantly different from untreated group (p<0.001, Student's t test)

Figure 8:
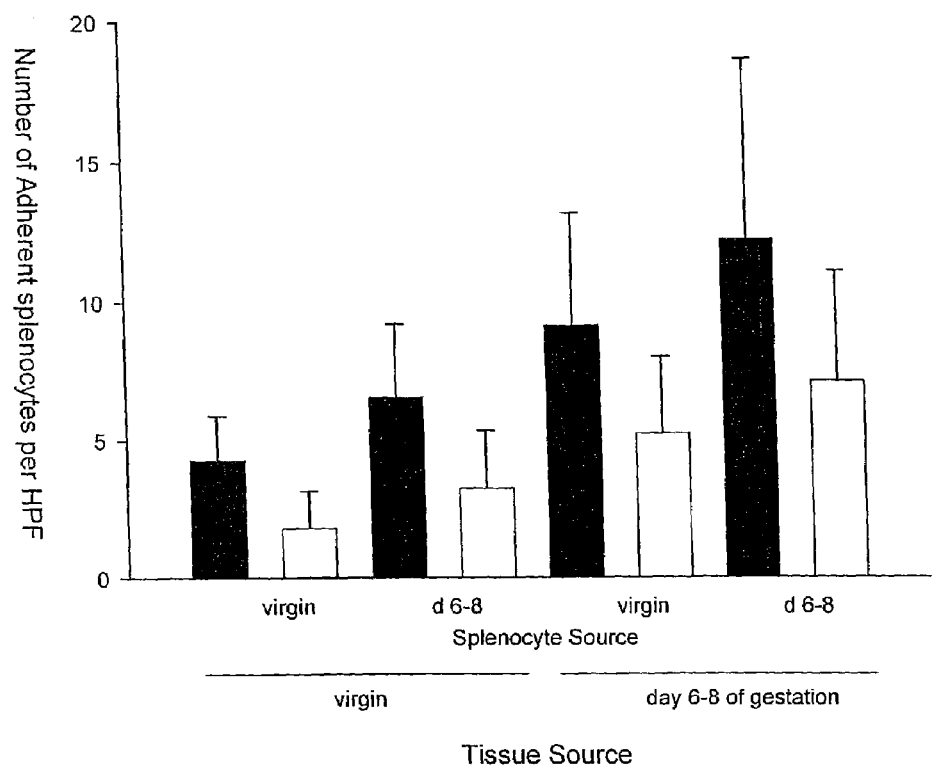

FIG. 8 is a bar graph showing data on the role of the L-selectin molecule in mediating adhesion between murine splenocytes and murine LN. Splenocytes were collected from both virgin and pregnant (day 6–8 of gestation) B6 mice and from virgin and pregnant (day 6–8 of gestation) $L-selectin^{-/-}$ mice. The cells were labeled with either CMFDA-green or CMAC-blue tracking dyes, mixed in a 1:1 ratio and overlaid onto frozen sections of LN from virgin ($1^{st}$ four bars) or pregnant (last four bars) B6 mice. Adherent green and blue cells were counted under fluorescence microscopy from 50 hp fields per experiment. The experiment was repeated using reversed fluors to label cells. Here, the results of both experiments are shown. The black bars represent the number of adherent B6 splenocytes±SD and the white bars show adhesion of L-selectin$^{-/-}$ splenocytes±SD. Adhesion of L-selectin$^{-/-}$ and B6 splenocytes was significantly different (p<0.001, ANOVA). Within groups, adhesion of splenocytes to tissue from pregnant animals as compared to tissue from virgin animals was significantly higher (p<0.001, ANOVA) and adhesion of splenocytes from pregnant animals was significantly higher than that of virgin animals (p<0.001, ANOVA).

Figure 9:
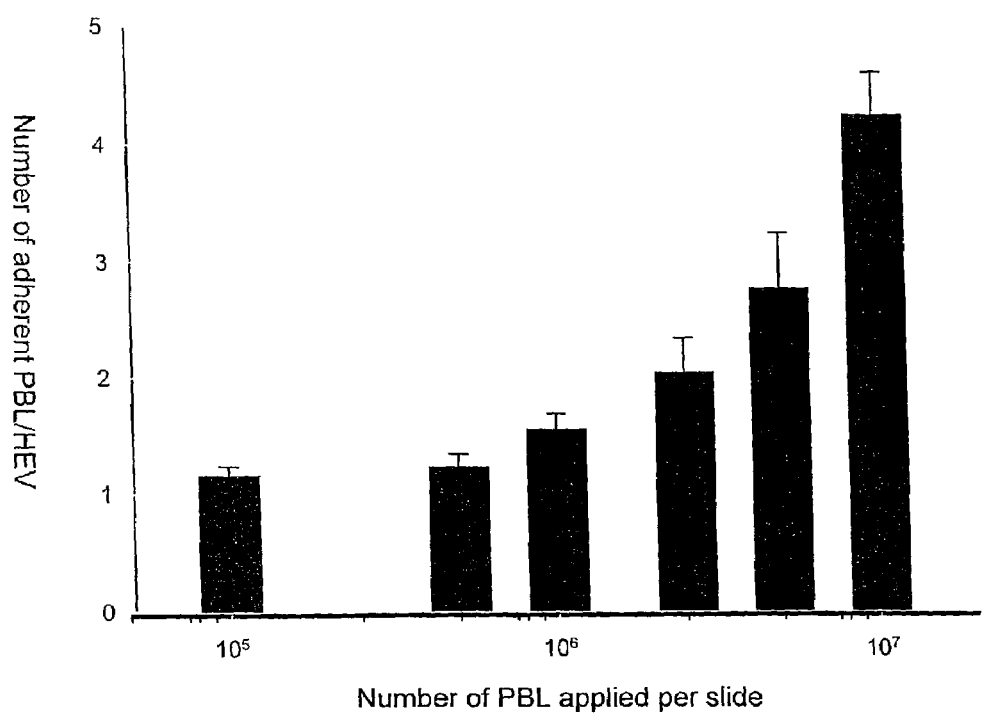

FIG. 9 is a bar graph illustrating the dose response of human lymphocytes to adhesion to LN from a pregnant mouse. Varying concentrations of cells ($10^7$ to $10^6$ cells/100 µl, as shown on the lower axis) were applied to frozen sections of LN, then after fixing and staining, the numbers of adherent cells were counted. The histogram shows the mean number of cells/HEV±SD of 200 HEV counted. A dose response was demonstrated and from this data, it was determined that $2.5 \times 10^6$ was the minimum number of cells required to detect a significant difference from adhesion of control cells.

Figure 10:
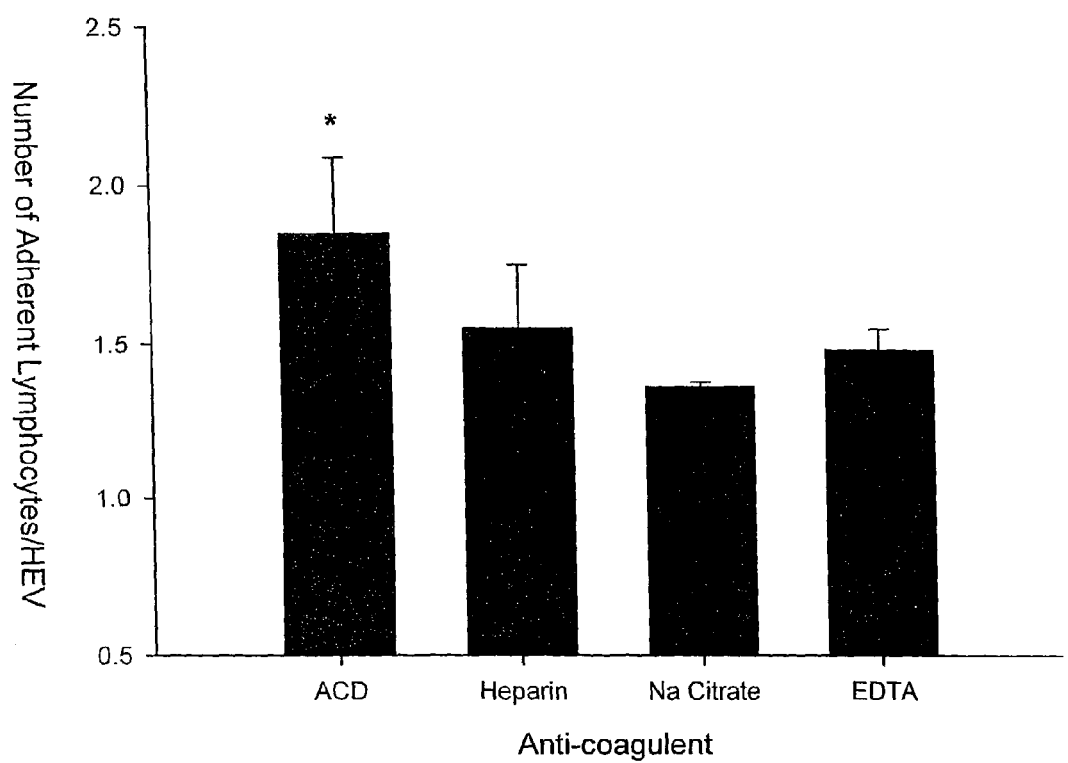

FIG. 10 is a bar graph depicting the effects of the type of anti-coagulant used in blood collection on the subsequent ability of human lymphocytes to adhere to LN from pregnant mice. Four samples of blood were collected into sterile tubes containing ACD, heparin, sodium citrate or EDTA from each of four subjects. Lymphocytes were isolated, washed thrice and used immediately in an adhesion assay. After fixing and staining, adherent lymphocytes were counted from each sample. The bars represent the mean number of lymphocytes counted per HEV from 200 HEV±SD.

Figure 11:
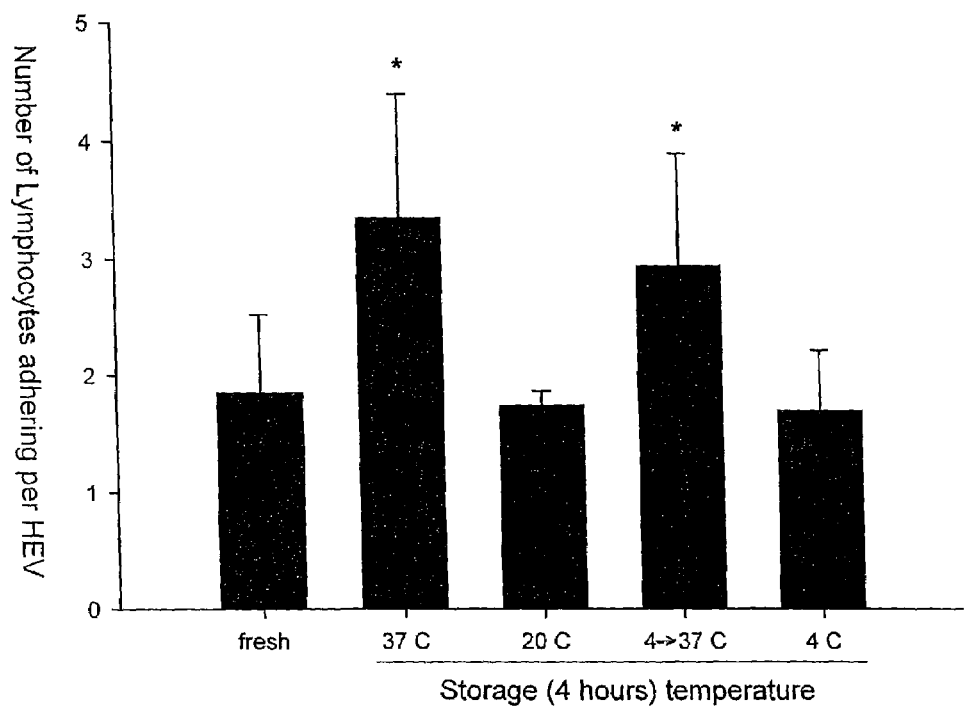

FIG. 11 is a bar graph summarizing the data collected on temperature effects on the ability of human lymphocytes to adhere to mouse LN. Four samples of blood were collected from 4 volunteer subjects, and incubated for 4 h either at 37° C., at 20° C., at 4° C. or at 4° C., then warmed to 37° C. After the incubation period, lymphocytes were isolated and used in an adhesion assay to LN from a pregnant mouse. Individual bars represent the mean number of adherent lymphocytes per HEV±SD of 200 HEV counted. * indicates significant difference from freshly isolated cells.

Figure 12:
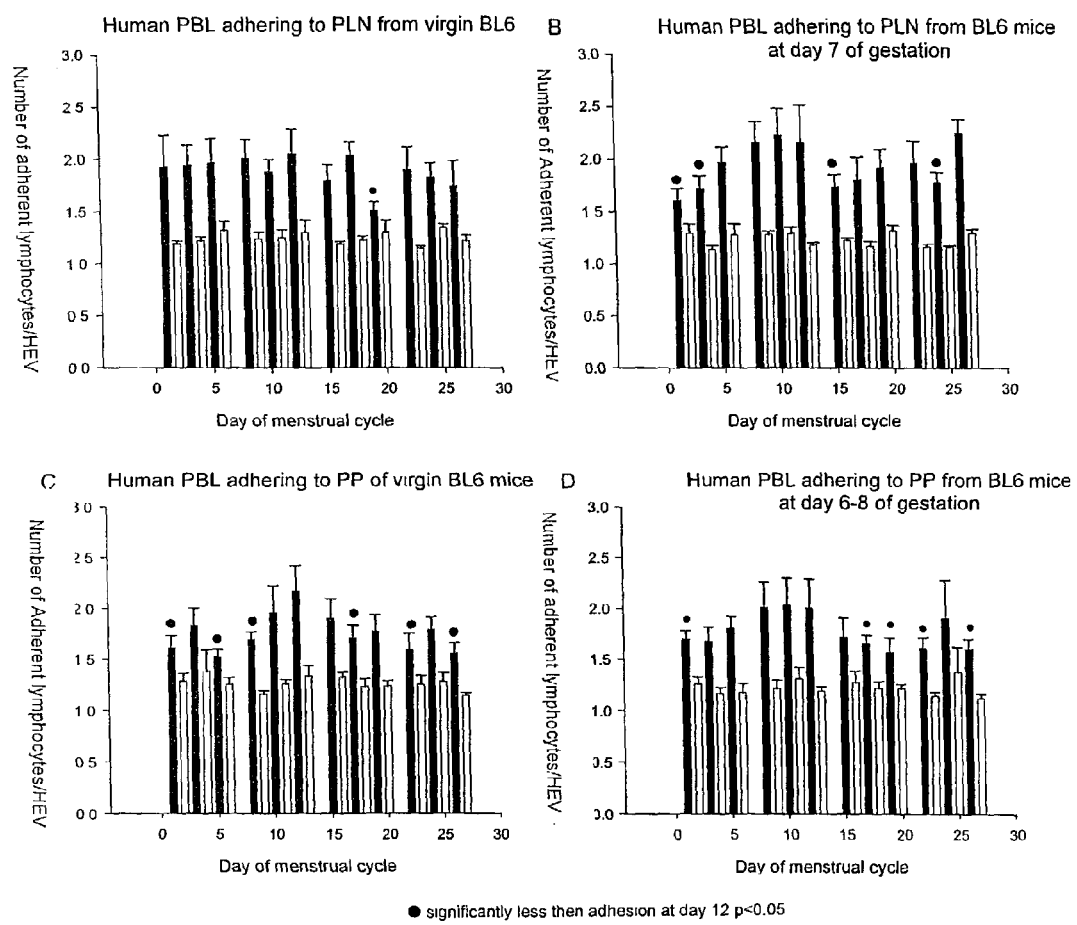

FIG. 12 shows histograms illustrating adhesion of human PBL taken over the course of a normal menstrual cycle to mouse tissues. Lymphocytes were collected from 7 normally cycling, informed and consenting adult women over the course of one menstrual cycle. In Panel A, it is shown that the adhesiveness of human peripheral lymphocytes (PBL) for HEV in PLN from virgin mice is not altered during the menstrual cycle but does respond to hormonal changes when contacted with LN from pregnant animals (Panel B) or with PP from both virgin (Panel C) and pregnant animals (Panel D). Black bars represent the mean±SD of bound lymphocytes/HEV. Open bars represent the mean numbers of adhering lymphocytes after treatment with an antibody to L-selectin. All blocking was statistically significant (p<0.05) using Student's t-test. * denotes significant decline in adhesion as compared to day 12 (peri-ovulation) of the menstrual cycle (p<0.05).

Figure 13:
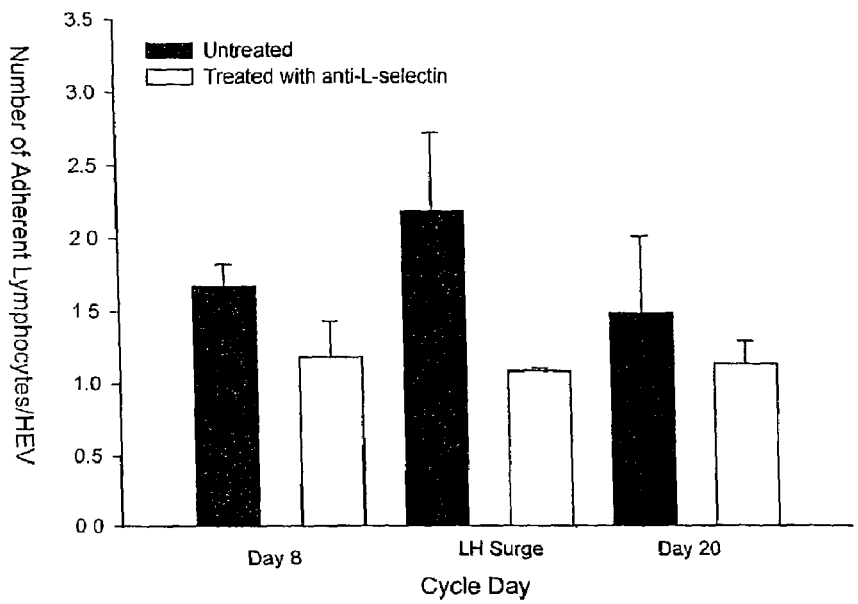
Figure 13:
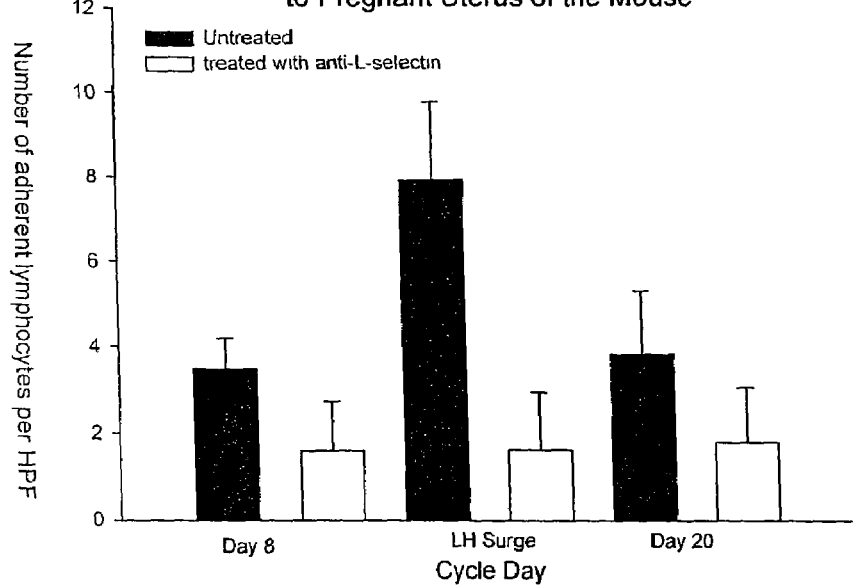

FIG. 13 shows bar graphs illustrating the adhesion of human PBL taken at 3 timepoints in the menstrual cycle to LN and uterine tissue from mice at day 8 of gestation. Six informed, consenting female volunteers of legal and reproductive age were recruited to monitor their cycle by basal temperature and use of an LH detection kit to pinpoint the LH surge and donate blood at cycle day 8, day of LH surge and at day 20. Serum samples were also obtained and used to measure concentration of E2, P4 and LH. Lymphocytes were isolated and used in an adhesion assay. Two hundred HEV were counted on LN sections and 50 HP (high power) fields were counted on uterine sections. In Panel A, the adhesion of lymphocytes from 3 timepoints of the menstrual cycle to LN are shown. Black bars represent the mean number of cells/HEV±SD. Open bars show adhesion when the lymphocytes were pre-treated with anti-L-selectin. In Panel B, samples of the same lymphocytes were applied to uterine tissue. Black bars represent mean number of adhered cells/HP field±SD. Open bars show mean number of adhered cells/HP field±SD when lymphocytes are pre-treated with anti-L-selectin.

Figure 1:
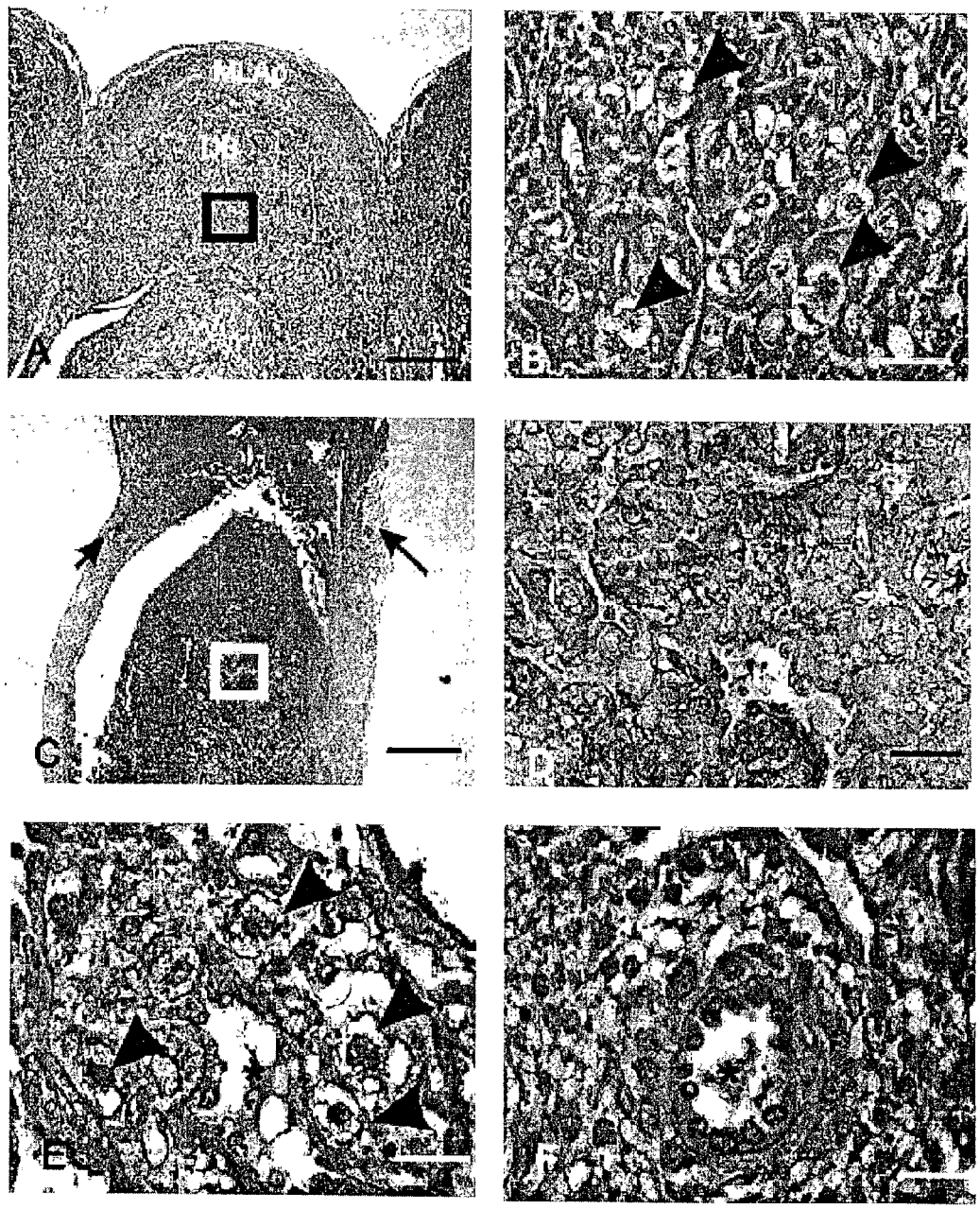
FIG. 1 shows photomicrographs of grafted uterine segments at day 10 of gestation. Boxed regions in A, C, E are enlarged in B, D and F. A&B) Lower and higher power images of a CD1 graft site in a CD1 recipient containing a normally developed implantation site including the mesometrial aggregation of lymphocytes (MLAp), decidua basalis (DB) and placenta (pl). B) show numerous, mature uNK cells (open arrowheads).C&D) Lower and higher power images of a SCID graft segment in a tgε26 recipient revealing development of a uterine stroma-derived deciduoma (DC). Image D is representative of the serial sections of the deciduomatae which contained no uNK cells. E) UNK (arrowheads) cells established within the decidual basalis by spleen cells from gestation day (gd 5) donors were mature granulated cells. F) Spleen cells from non-pregnant donors did not generate uNK cells in the 10 day assay protocol. The blood vessel (asterisk) is an unmodified decidual spiral artery. MT, mesometrial triangle, DB, decidua basalis, pl placenta. A–F stained with PAS. Bars in A&C represent 400 μmm; in B, 40 μmm and in D–F, 25 μmm.

DETAILED DESCRIPTION OF THE INVENTION (i) Method of Monitoring the Menstrual Cycle and/or Pregnancy in a Female Prior to the present study, it was unclear whether the immediate precursors of uNK (pre-uNK) cells self-renew within uterus or are recruited from the periphery. A series of experiments in which uterine horns from wild-type mice were transplanted to NK-cell deficient mice demonstrated that precursors of uterine NK cells do not reside within the uterus, but re-populate. Subsequent investigations of engraftment of lymphocytes isolated from various hematopoietic tissues of wild-type mice into NK cell deficient mice established that the majority of NK cells which populate the pregnant uterus were recruited from the spleen. Splenic cells lacking the chemokine receptors, CCR2 and CCR5 were recruited equally to the wild-type spleen, indicating that alternative chemokine receptors are used by NK cells to home to the uterus (FIG. 1).

Lymphocyte recruitment into tissues requires adhesive interactions with vascular endothelium. This was assessed by examining adhesion of human lymphocytes to frozen mouse tissue sections under shear. The Stamper-Woodruff assay of cell adhesion to frozen tissue sections takes advantage of the fact that human lymphocytes bind to murine adhesion molecules[70]. Human lymphocytes were prepared as indicator cells from single blood donor buffy coats purchased from the American Red Cross. Consistent results have been obtained with 20 donors although no information is available regarding sex or possible menstrual cycle stage of these donors. For uterine tissue sections, pregnancy induced a dynamic increase in L-selectin and alpha4 integrin-dependent adhesion of CD56$^{bright}$ NK cells that became localized to the developing decidua basalis (DB). Most of the binding was blocked by monoclonal antibody (MAb) against L-selectin. These studies are the first to demonstrate dynamic changes in endothelial adhesion associated with pregnancy. These data support a model in which the dramatic increases in human and murine uNK cells during decidualization result from vascular recruitment of precursor cells from secondary lymphoid organs.

The same lymphocyte preparations were assessed for adhesion to murine Peyer's Patches, pancreas and uterine tissue sections. Dynamic changes similar to those in lymph nodes were found in Peyer's Patches. Importantly, no pregnancy-associated changes occurred in pancreas, showing pregnancy regulates leukocyte endothelial interactions in selected tissue micro-environments.

Adhesion was infrequent to non-pregnant uterus, (between endometrium and myometrium mesometrially and antimesometrially) but high numbers of human cells localized to decidua basalis of pregnant uteri. A further remarkable finding was that 10–15% of cells adhering to pregnant uteri were very large lymphocytes, non-adherent to virgin uterus, LN, PP or pancreas. The inventors predicted these would be $CD56^{bright}$ NK cells. Buffy coat cells were prelabelled with anti-CD56 to identify NK cells and then applied to mouse tissues. No $CD56^{bright}$ cells adhered to non-pregnant uterus, but both large and small $CD56^{bright}$ lymphocytes specifically localized to decidual basalis (gd 6 and 10) in high numbers. Significantly, numerous clusters of large $CD56^{bright}$ were noted in the gd 6 uteri. The number of bound lymphocytes/cluster was markedly increased on gd 10 uteri. These clusters of adherent cells were not observed in uteri from hormone-treated mice (see below) or in peripheral tissues of any of the mice investigated.

These innovative and novel results clearly suggest that both small lymphoid precursors and mature uNK cells circulate in human blood and move to the uterus, due to changes in uterine endothelium. This agrees with recent work which mapped endothelial cell expression of adhesion molecules across murine implantation sites and showed a unique, VCAM-1 rich, microdomain in decidua basalis that excluded all lymphocytes except mouse uNK cells.[39, 40]

The effect of estrogen and progesterone, gestational hormones associated with the menstrual cycle and with early gestational success, on ability of endothelial cells and/or lymphocytes to interact functionally was investigated in experiments where the mouse providing the lymphoid tissue source is treated with the hormone. Murine splenocytes, human lymphocytes and $\alpha 4$ integrin$^+$, L-selectin$^-$ TK-1 cells were used in these assays. It was found that estrogen or progesterone alone or in combination were equivalent to pregnancy in promoting lymphocyte-L-selectin-dependent and $\alpha 4$ integrin-dependent adhesion to endothelium under shear flow conditions. Endothelium was not universally altered in the estrogen-treated females as there was no increase in adhesion of blood lymphocytes, or of TK-1 cells to pancreas endothelium.

Estrogen also altered endothelium cell-lymphocyte interactions in assays using uterine tissues. The percentage of $CD56^{bright}$ cells in the starting human lymphocyte preparation was 2–3%. By interaction with uterine tissue (non-pregnant) alone, the percentage of $CD56^{bright}$ cells was greatly enriched (2.5 fold) to 10%. There was further enrichment to 70% if the uterine tissue was from a mouse receiving hormone therapy and this enrichment was not different to that seen for a pregnant uterus. Thus, estrogen induced changes in the uterine endothelium were proven to promote interactions specifically with human $CD56^{bright}$ cells, the cell subset that normally homes to the uterus in pregnancy.

In a similar series of experiments, it was determined that progesterone, independent of estrogen, can modify lymphocyte-endothelial cell interactions. Thus, human lymphocytes were shown to have enhanced L-selectin-dependent binding (above that measured in tissues from non-pregnant or ovariectomized placebo treated females) to peripheral lymph node endothelium from a mouse receiving progesterone replacement therapy. Also, the $\alpha 4$ integrin-expressing TK1 cell line was shown to have enhanced, progesterone-dependent, and $\alpha 4$ integrin-dependent, binding to endothelium in Peyer's Patches. Adhesion of human $CD56^{bight}$ cells to uterine gestational tissues was also promoted in ovariectomized, progesterone-treated mice.

The dual treatment of the ovariectomized mice with estrogen and progesterone did not enhance the interactions of human $CD56^{bright}$ cells with uterine stroma from the treated mice beyond those seen with treatment using only single steroid therapy. The results with mice receiving dual treatment with estrogen and progesterone as well as induction of uterine decidua indicate that the enhanced interactions between human $CD56^{bright}$ cells and uterine stroma from the treated mice in the presence of estrogen and/or progesterone occur independently of whether or not the uterus has undergone decidualization of its stromal cells.

The clusters of large $CD56^{bright}$ cells that adhered to pregnant uteri at gd 6 and later, were not seen in experiments involving the adherence of lymphocytes to uteri from hormone-treated mice, nor in experiments involving adherence of lymphocytes to peripheral lymph tissues.

Further results have been obtained using murine lymphocytes isolated from the spleen to replace human blood lymphocytes. Mouse uterine tissue, lymph node, intestinal Peyer's Patches and pancreas have been used as the adhesion substrate. Seven different types of mice have been used in these adhesion experiments. These mice were 1) normal cycling virgin young adult females; 2) naturally mated, gestationally timed primiparous females; 3) ovariectomized virgin adult females treated with a placebo; 4) ovariectomized virgin adult females receiving estrogen replacement therapy; 5) ovariectomized virgin adult females receiving progesterone replacement therapy; 6) ovariectomized virgin adult females receiving combined estrogen plus progesterone replacement therapy; and 7) ovariectomized virgin adult females receiving combined estrogen plus progesterone replacement therapy plus induction of uterine decidua. Using lymph nodes from only non-pregnant mice as a substrate, it was shown that splenocytes collected from pregnant mice or hormone treated mice were more adhesive to non-pregnant lymph node endothelium than the splenocytes isolated from non pregnant mice (FIG. 7). Further, the lymphocytes from mid pregnancy (gd 10) were more adhesive than those from the first trimester (gd 6). Antibody blocking of the Peripheral Node Addressin (PNAd) receptor reduced adhesion, confirming involvement of the ligand for this receptor, L-selectin, as a key molecule in the process. The level of adhesiveness of the lymphocytes from pregnant mice and hormone-treated mice was the same as those seen in fever range hyperthermia. Thus, the elevated adhesion to blood vessel endothelium (a requisite for moving a cell from the circulation and into a tissue) is a combined result of the effect of pregnancy on both organ specific endothelium and on the lymphocytes themselves. This interaction was also shown to involve $\alpha 4$ integrin-mediated pathways.

Therefore, it has been shown that pregnancy, estrogen replacement therapy and progesterone replacement therapy each promote functional interactions between lymphocytes and endothelium of the uterus and the lymphoid organs. Endothelium from other sites, such as pancreas is not altered. This predicts that the controlled ovarian stimulation used for oocyte collection for women undertaking embryo transfer could significantly modify or disrupt the movement of NK cells into the uterus. It has also been shown that there are separate actions of pregnancy or hormone replacement that independently modify the endothelium or the lymphocyte population. Further, it has been confirmed that $CD56^{bright}$ human blood lymphocytes (the human uterine phenotype) are enriched when interacting with uterine endothelial cells from non pregnant uteri and very strongly enriched when interacting with uterine endothelial cells from pregnant uteri. It has also been shown that the $CD56^{bright}$ cells form clusters on uteri from pregnant mice, but not on uteri from hormone-treated mice or in peripheral tissues. The formation of clusters of lymphocytes on uteri tissue from a pregnant animal may provide a significant means to monitor the luteal phase of a menstrual cycle and/or a pregnancy in a female. Finally it has also been shown that a technical assay for studying the interaction between lymphocytes and endothelium from uterine and/or lymph nodes is valid for many blood donors and that the assay gives consistent results when applied to studies of gestational lymphocytes and endothelium.

In experiments using peripheral blood lymphocytes (PBL) from healthy, female volunteers of reproductive age in a time-based study of the effects of the menstrual cycle on the adhesive properties of PBL to adhesion molecules expressed on vascular endothelium from a mouse, the present inventors have found that, under normal conditions, adhesion peaks on the day of luteinizing hormone (LH) surge, which occurs about mid-way through the menstrual cycle, in the peri-ovulatory period. This confirms that the assay of the invention may be used to monitor a menstrual cycle and/or pregnancy in a female in order to assess the female for optimum conditions for sustaining a pregnancy.

Accordingly, the present invention provides a method of monitoring a menstrual cycle and/or pregnancy in a female by detecting the adhesion of lymphocytes from the female with uterine or lymphoid tissue from a pregnant animal or from a non-pregnant animal that has been treated with gestational hormones. In particular, the method can be used to determine whether a uterine environment is conducive for sustaining a pregnancy and is recognized by the immune system of a woman trying to conceive. This recognition will indicate that her lymphocytes will home appropriately to her uterus, optimizing the uterine environment for her embryo. The greater the adhesion of the lymphocytes, in particular the $CD56^{bright}$ NK cell subset, the better the uterine environment is to sustaining a pregnancy. Also the greater the number of clusters of $CD56^{bright}$ NK cells adhered to uterine tissue from a pregnant animal, the better the uterine environment is to sustaining a pregnancy. The method will have particular utility in women having trouble conceiving, women experiencing habitual miscarriages and women undergoing in-vitro fertilization (IVF). In such cases the assay of the invention can be used to determine if the problems in conceiving or maintaining a pregnancy are related to problems in lymphocyte trafficking to the uterine environment. The method of the invention can also be used to monitor an early pregnancy wherein the greater the adhesion the greater the chance of sustaining the pregnancy. Accordingly, in an embodiment, the method of the invention is used to monitor changes in the ability of a lymphocyte from a female to home or adhere to a uterus, the changes being induced by the menstrual cycle and/or a pregnancy in the female.

In a further embodiment, the method or assay of the invention comprises:

(a) obtaining lymphocytes from the female; and (b) contacting the lymphocytes with uterine or lymphoid tissue from a pregnant animal or from a non-pregnant animal that has been treated with gestational hormones; and (c) detecting the adhesion of the lymphocytes with the uterine or lymphoid tissue.

The female can be any female animal wherein one desires to monitor an estrous or menstrual cycle or pregnancy. The female is preferably a human female.

The lymphocytes can be obtained from any sample from the female and are preferably obtained from blood or fractions thereof. The lymphocytes used in the assay are preferably peripheral blood leukocytes that may be tagged to identify the natural killer cell subset. Most preferably, the human lymphocytes are $CD56^{bright}$ natural killer cells.

The term "uterine or lymphoid tissue" includes sections or homogenates of the tissue, or adhesion molecules derived from these tissues or tissue homogenates, or cells transfected with adhesion molecules derived from these tissues or tissue homogenates. The uterine or lymphoid tissue can be from any animal and is preferably from a mouse, rat, golden hamster, guinea pig, rabbit, human or other species in which decidual tissues develops in the pregnant or pseudopregnant uterus. The uterine tissue is preferably from the decidua basalis. The lymphoid tissue can be from any lymphoid tissue and is preferably from the lymph node or Peyer's Patches. In the assay, histological sections, homogenates of the tissue or molecules derived from the tissue, either adhered to a substrate or expressed in a cell line, may be used. The tissue, homogenates, molecules or cells may be placed on or adhered to a coverslip or microtitre plate to which the lymphocytes can be directly applied. Examples of adhesion molecules that may be used in the method of the invention include cell adhesion molecules and integrins. The expression of adhesion molecules in cells can be carried out using well known recombinant DNA technology (suitable methods for transforming and transfecting host cells can be found in Sambrook et al. Molecular Cloning: A Laboratory Manual, 2nd Edition, Cold Spring Harbor Laboratory press (1989), and other laboratory textbooks). It is preferred for the adhesion molecules to be expressed on the surface of such cells. An example of a cell that is suitable for the expression of such molecules is Bosco's cell line.

The term "gestational hormones" refers to any hormone associated with gestation including luteinizing hormone, chorionic gonadotropin, estrogen and/or progesterone. More than one gestational hormone may be used to treat the animal. Preferably, the gestational hormone is estrogen or progesterone, or a mixture thereof.

The term "treated with gestational hormones" as used herein means to administer an effective amount of one or more gestational hormones to the animal. In this context, an "effective amount" is an amount sufficient to induce decidualization in the animal. The use of gestational hormones to induce decidualization in rodent models is well known in the art.[83]

In embodiments of the invention, greater adhesion of the lymphocytes, in particular the $CD56^{bright}$ NK subset, indicates a better uterine environment for sustaining a pregnancy. The term "greater adhesion of lymphocytes" means the adhesion of lymphocytes from the female is greater with lymphoid or uterine tissues from a pregnant animal, or a non-pregnant animal that has been treated with gestational hormones, than with a control. A suitable control may be, for example, the adhesion of lymphocytes from the female with uterine or lymphoid tissues from a non-gestational-hormone-treated, non-pregnant animal or a suitable non-lymphoid or non-uterine tissue, for example, endothelium from the pancreas. Other suitable controls include: 1) the adhesion of lymphocytes from a non-pregnant, non-gestational-hormone-treated animal, or from a male, to uterine or lymphoid tissues from a non-gestational-hormone-treated, non-pregnant animal or a suitable non-lymphoid or non-uterine tissue, for example, endothelium from the pancreas; and 2) the adhesion of lymphocytes from a non-pregnant, non-gestational-hormone-treated animal, or from a male, to uterine or lymphoid tissues from a gestational-hormone-treated or a pregnant animal The term "detection" as used herein refers to any qualitative or quantitative determination or assessment of lymphocyte adhesion to target tissues. In order to detect adhesion of the lymphocytes with the uterine or lymphoid tissue any known method can be used. For example, lymphocytes may be enumerated by microscopic observation as described in Example 1, either by staining with, for example, toluidine blue, or using a fluorescent label. Automated scoring based on differential spectroscopy or calorimetric measurement of stained lymphocytes may also be used.

In another embodiment of the invention, the method or assay of the invention comprises:
  (a) obtaining lymphocytes from the female; and
  (b) contacting the lymphocytes with uterine tissue from a pregnant animal; and
  (c) detecting the number and/or size of clusters of lymphocytes adhered to the uterine tissue.

In embodiments of the invention, a greater number and/or total size of clusters of lymphocytes from the female, in particular the $CD56^{bright}$ NK subset, adhered to decidualized uterine tissue from a pregnant animal indicates a better uterine environment for sustaining a pregnancy. The term "greater number and/or total size of clusters of lymphocytes" means the number and/or total size of clusters of lymphocytes from the female adhered to decidualized uterine tissue from a pregnant animal is greater than the number of clusters of lymphocytes from the female adhered to a control, for example to a non-pregnant uterus. As used herein the term "cluster(s)" refers to a group of more than 5 lymphocytes adhered in a single location, in contact with at least 1 other lymphocyte. Individual clusters may be as large as several hundred cells in contact.

The invention also includes the identification of lymphocyte subsets involved in the adhesion and to the determination of the effect of pituitary or ovarian hormones on the interactions between lymphocytes and uterine or lymphoid endothelium. The invention further relates to the determination of the effect of controlled ovarian hyperstimulation (COH) with fertility drugs on the interaction between the lymphocytes and the uterine or lymphoid endothelium.

(ii) Kits

The development of the method of the invention allows the preparation of kits for use in monitoring the menstrual cycle and/or a pregnancy of a female. The kits would comprise the reagents suitable for carrying out the methods of the invention, packaged into suitable containers and providing the necessary instructions for use.

Accordingly, the present invention includes a kit for monitoring a menstrual cycle and/or pregnancy of a female comprising uterine or lymphoid tissue, wherein the tissue is from a pregnant animal or a non-pregnant animal that has been treated with gestational hormones. Preferably the tissues are mounted on a solid support. For example, tissues may be adhered to a coverslip or a microtitre plate.

The kits may also include reagents to separate lymphocytes from blood and/or reagents, for example antibodies, for tagging or separating the desired lymphocyte subset, for example $CD56^{bright}$ natural killer cells, from the blood or the lymphocytes.

The kits may also include reagents to perform a control. In an embodiment of the invention, the reagents to perform a control comprise uterine or lymphoid tissues from a non-gestational-hormone-treated, non-pregnant animal or a suitable non-lymphoid or non-uterine tissue, for example, endothelium from the pancreas. In another embodiment of the invention, the reagents for performing a control comprise lymphocytes from a non-pregnant, non-gestational-hormone-treated female or a male.

With particular regard to assay systems packaged in "kit" form, it is preferred that assay components be packaged in separate containers, with each container including a sufficient quantity of reagent for at least one assay to be conducted. A preferred kit is typically provided as an enclosure (package) comprising one or more containers for the within-described reagents.

The reagents as described herein may be provided in solution, as a liquid dispersion or as a substantially dry powder, e.g., in lyophilized form. Usually, the reagents are packaged under an inert atmosphere.

Printed instructions providing guidance in the use of the packaged reagent(s) may also be included, in various preferred embodiments. The term "instructions" or "instructions for use" typically includes a tangible expression describing the reagent concentration or at least one assay method parameter, such as the relative amounts of reagent and sample to be admixed, maintenance time periods for reagent/sample admixtures, temperature, buffer conditions, and the like.

The following non-limiting examples are illustrative of the present invention:

EXAMPLES

Example 1

Identification of the Source of NK Cells in the Pregnant Uterus

Goals of Example 1 were i) to determine if uterus self renews uNK cells and ii) to examine peripheral lymphoid tissues as sources for pre-uNK.

Materials and Methods

Animals

Immunocompetent mice (randombred CD1, Charles River Laboratories, St. Constant, PQ), C57BI/6J (B6) and C57BI/6×129/J F1 (F1, Jackson Laboratories, Bar Harbor, Me.)) were housed under standard husbandry in the Central Animal Facility, University of Guelph. Immunodeficient mice, (randombred ICR- scid/scid (SCID; NK+,T−,B−, Taconic, Germantown, N.Y.), tgεε26 ($H-2^{k/b}$; NK−,T−,B+) and RAG-$2^{-/-}$/γ$c^{-/-}$ ($H-2^b$; NK−,T−,B−) were housed in the University of Guelph's barrier-husbandry facility. Both tgεε26 or RAG-$2^{-/-}$/γ$c^{-/-}$ lack uNK cells and are referred to as uNK cell deficient.[17] Mice ablated for CCR2 ($H-2^{k/b}$) and CCR5 ($H-2^{k/b}$)[71,72] were bred at University of Texas, Austin, Tex. and shipped to Guelph. Females over 8 wks of age were used, unless stated and, if bred, were mated to males of the same strain. Gd 0 was the morning of copulation plug detection. Euthanasia was by $CO_2$ followed by cervical dislocation.

Uterine Segment Transplantation

Uterine segments (10 or 5 mm), trimmed of mesentery and vessels, were grafted from virgin donors to virgin recipients in an orthotopic manner that preserved both cranial-caudal and mesometrial-antimesometrial orientations. For autotransplantation (n=2), CD1 females were anaesthetized (0.35 ml of xylaxine (20 mg/ml) and ketamine (100 mg/ml)) and the donor horn was reanastomosed with simple interrupted 8-0 Vicryl (Polysorb®, Norwalk, Conn.) sutures. For all other grafting, donors (CD1 or SCID) were euthanised while recipients (tgεe26 or CD1) were anaesthetized as above. Recipient horns were cut at their midpoint and donor tissue was inserted and anastomosed. No vascular anastomosis was attempted. The abdomen was closed surgically. After 7 days, recipients were paired for breeding and euthanised at gd 10.

Thymic Engraftment

Thymuses were dissected from non-pregnant or pregnant (gd 3, 5) adult or neonatal (48 hr) B6 mice and grafted under the renal capsule of anaesthetized gd 0 RAG-$2^{-/-}/\gamma c^{-/-}$.

Adoptive Transfer of BM, LN or Splenocytes

Bone marrow (BM) and spleen cell (SC) donors were non-pregnant or pregnant SCID mice while lymph node (LN) donors were B6 (gd 3, 5 or 7). As pregnancy changes cellularity of these organs, one donor was used per recipient, pooling donors if several mated recipients were available on the same day. Uteri from all gd 3 donors were flushed to confirm pregnancy by detection of pre-implantation blastocysts. BM was flushed from femurs and tibias of each donor. Microscope-aided dissection was used to harvest peripheral (P) LN (9 superficial and 3 pelvic LN/donor) that were pooled and the mesenteric (M) LN chain. LN and spleens were dissociated mechanically. PBS (400 μml with/without cells) was infused via tail veins into gd 0 tgεe26 or RAG-2-/-/γc-/- recipients who were sacrificed on their gd 10.

Morphometric Analyses

Abdominal contents were examined grossly, then uteri were dissected, fixed in Bouin's solution, processed routinely for paraffin embedding, serially sectioned at 7 μmm (transversely for normal uteri and longitudinally for surgically manipulated uteri) and stained with Haematoxylin and Eosin (H&E) for routine histopathology or Periodic Acid Schiff's (PAS) for uNK cell enumeration. Eleven central tissue sections from each implantation site were scored as previously described.[18] One $mm^2$/section was analysed in each mesometrial microdomain, decidual basalis (DB) and the mesometrial aggregation of lymphocytes (MLAp). Circular smooth muscle was used as the boundary between these. When the MLAp was absent or rudimentary, mesometrial triangle (MT) rather than MLAp is the term used to describe the scored region. For longitudinally sectioned uteri, those containing a conceptus were scored as above. Uteri containing a deciduoma were scored in two independent 1 $mm^2$ areas of 10 of the serial sections separated by 42 μmm to avoid duplicate counting of uNK cells which can reach 40 μmm by gd 10. Means and standard deviations of uNK cells/$mm^2$, p values and Student-Newman-Keuls test for ANOVA were conducted using PC-SAS 6.12 for Windows (SAS Institute Inc., NC).

Results

Assessment of uNK Cells in Uterine Segment Transplants

Feasibility of orthotopic uterine grafting was assessed in autologously grafted CD1 mice using grafts of 10 mm (n=3) and 5 mm (n=4). The longer grafts showed gross full-length necrosis while the shorter grafts were viable. All recipients of the 5 mm grafts were pregnant with three grafts containing implantation sites and the fourth a deciduoma (Table 1). Typical uNK cells with 16–45 μm in diameter and containing 9–25 PAS reactive granules/cell were found in these decidualized grafts (FIG. 1A&B). Thus, orthotopically-grafted mouse uterus supports uNK cell differentiation. Next, 5 mm uterine segments were grafted from uNK cell competent CD1 or SCID donors into NK/uNK cell deficient tgεe26 recipients (n=7). Two females mated but were not pregnant at euthanasia, despite grossly and histologically normal grafts. Five recipients were pregnant and each grafted segment contained a large deciduoma indicative of viable, hormonally-responsive tissue. By serial section analysis, neither the deciduomatae in donor tissues nor implantation sites in host tissues contained uNK cells (FIG. 1C&D). Thus, the donor segments did not contain self-renewing pro/pre-uNK cells that could differentiate in situ or migrate to adjacent implantation sites.

Development of uNK Cells from Thymus, BM, LN and SC

At gd10 in normal and SCID mice, range in uNK cell frequency is 27–53 cells/$mm^2$ in DB and 72–129 cells/$mm^2$ in MLAp (Table 2). UNK cell sizes in B6 mice ranged from 11–20 μm (average 14.3±2.9) and in SCID mice 11–27 μm (mean 15.9±4.0). All uNK cells were granulated and contained 8–35 (mean 18.0±8.2) and 5–30 granules/cells (mean 19.4±9.0) in B6 and SCID mice, respectively. Uterine segment transplantation suggested that migration of pre-uNK cells accounts for filling of these microdomains. Peripheral lymphoid tissues were assessed for pre-uNK cells by grafting to mated, uNK cell deficient mice. Thymic engraftment generated limited numbers of uNK cells at gd 10 (Table 2). There were no statistical differences in reconstitution of DB or MT by thymuses of different ages or from different donor pregnancy states (p>0.05). BM from non-pregnant or 3 early times of pregnancy also gave low level uNK cell reconstitution in all recipients (Table 2). No significant differences were found in uNK cells/$mm^2$ in DB or MT between the BM donor groups (p>0.05). MLN failed to reconstitute uNK cells while implantation sites in recipients of PLN showed MLAp development. Both MLAp and DB of PLN grafted mice contained mature uNK cells. Implantation sites in uNK cell deficient mice receiving SC from pregnant donors also showed histological development of MLAp and high levels of uNK cells in both MLAp and DB. However, if the SC donors were not pregnant, uNK cell reconstitution was much lower (p<0.001) in both microenvironments. As shown in FIG. 1(E&F), levels of engraftment resulting from inoculation of SC from pregnant donors was sufficient to modify the decidual spiral arteries. In sharp contrast, host arterial vasculopathy persisted in recipients of SC from non-pregnant donors. For all SC donors, uNK cells were present at higher frequencies in the MLAp than in DB (p<0.01), a typical gd 10 pattern in normal mice. Morphological assessment of graft-derived uNK cells showed that uNK cells derived from thymus, BM, LN and SC were similar in size (14.5±4.0, 15.6±4.5, 18.7±7.5 and 13.9±4.7 μm, respectively) and in numbers of granule/cell (12.8±5.8, 15.6±5.5, 20.5±11.9, 17.8±7.7, respectively). These morphology were identical to gd 10 uNK cells in unmanipulated B6 and SCID mice, implying equivalent maturity.

To test the role of specific chemokines expressed by the pregnant uterus on pre-uNK cell recruitment, mated RAG-2-/-/γc-/- females were infused with SC from pregnant (gd 3 or 5) CCR2-/- or CCR5-/- mice. High levels of uNK cells were found in all recipients that did not differ numerically or morphologically from uNK cells in gd-matched, F1 controls (Table 2). These data indicate that the chemokines MIP-1 α, MCP-1 and RANTES are not essential for uterine recruitment of pre-uNK cells.

Discussion

This is the first comprehensive study, in any species, to address the source of the immediate precursors of uNK cells in a pregnant adult. Availability of NK/uNK cell deficient mice that reliably carried pregnancies was central to the study's success. Following transplantation of uterine segments from NK+ mice into NK−/uNK− mice, no uNK cells were found in decidual tissue within the grafts or at any of the implantation sites in host tissue. The latter observation excluded migration of pro/pre-uNK cells from the graft segments into host tissue and established that mouse uterus does not contain self-renewing pro/pre-uNK cells. Uterine and oviductal grafts, used in published studies, may have scarred and died due to problems of excessive length, inadequate perfusion and/or immune rejection. The choice of an immune deficient host eliminated host versus graft rejection. Early graft versus host disease was not a problem as allografts from CD1 were as equally viable and hormone responsive as T cell deficient SCID allografts. Duration of the transplantation experiments was shorter (17 days) than mouse gestation (19–20 days), permitting the conclusion that uterine recruitment likely occurs during gestations. Previous grafting of mated, immunocompetent mice with virgin uterine tissue in sealed diffusion chambers showed that uterus has some pre-uNK cells with a 12 day maximum survival time.[74]

To explain the dramatic rise in human uNK cells during decidualization some authors suggest that uNK cells self-renew in the uterus,[75] while others suggest precursor trafficking from BM.[76] The present studies indicate that both ideas maybe incorrect. In adoptive transfers, BM was identified as only a minor pre-uNK cell source. Despite the known and observed involution of BM (Table 2), there was no loss in progenitors able to populate uterus with uNK cells, during the first trimester of pregnancy. Because pregnancy alters lymphocyte frequency in organs, transferred cells always included all of the nucleated cells recovered from a defined tissue on the specified gd. This design approximates the physiological situation better than transfer of fixed cell numbers. Levels of uNK cell generation from thymus were also low and independent of donor age or pregnancy status. However, the present results show for the first time that thymus retains its capacity for NK cell generation into adulthood.

Not all LN had transplantable pre-uNK. MLN did not hypertrophy and lacked pre-uNK. Cell yields from other LN or LN chains were too low to assess each as a source of pre-uNK cells; thus, PLN were pooled. Hypertrophy was anticipated in the pelvic LN draining the uterus[77] but was not measurable in the cell pool. Transplantable pre-uNK were present in PLN. However, the cellular composition of the pooled LN is probably not homogeneous because development of some PLN (i.e. cervical, included in the pool) is regulated in a manner analogous to MLN development.[78] Further study would be required to precisely define the PLN-containing transplantable pre-uNK.

Spleen contained pre-uNK cells that were mobilized for relocation to the uterus by pregnancy. In comparison to non-pregnant donors, spleen cell numbers doubled in pregnant donors while numbers of uNK cell progeny increased 4–47× (Table 2). This suggests that numerical alterations are not the sole pregnancy-induced changes in SC accounting for uNK cell reconstitution. The developmental stages of hematopoietic cells which move into the uterus are not yet known. Because uNK cells differentiating from thymus, BM, LN and SC are identical morphologically and morphometrically and match those in gd 10 unmanipulated, genetically normal mice, the cells which moved into the uterus from these tissues were probably at relatively similar stages of differentiation. Alternatively, uNK cells may differentiate rapidly and cells at various pro/pre-uNK stages may have had sufficient time to complete differentiation under the experimental conditions described herein. The heterogeneity in size of human lymphocytes adhering to murine uterus suggests that circulating cells at more than one stage of differentiation/activation may have uterine homing potential. Lack of CCR2 or CCR5 did not reduce pre-NK cell homing from spleen to uterus despite high levels of CC chemokine expression in pregnant human and mouse uteri[79,80] suggesting that these chemokines target other cell types, and/or that there is a redundancy in uterine chemokines adequate to recruit pre-uNK cells through other receptors.

Example 2

Cell Adherence to Murine Tissue Sections Under Shear and Effect of Hormones of this Adherence Goals of Example 2 were i) to determine whether human peripheral blood lymphocytes (PBL) recognize and bind to adhesion molecules expressed on the vascular endothelium of the mouse uterus and lymphoid tissue and ii) to determine whether pregnancy/pregnancy hormones altered this recognition.

Materials and Methods

Mice and Tissue Dissections

Figure 2:
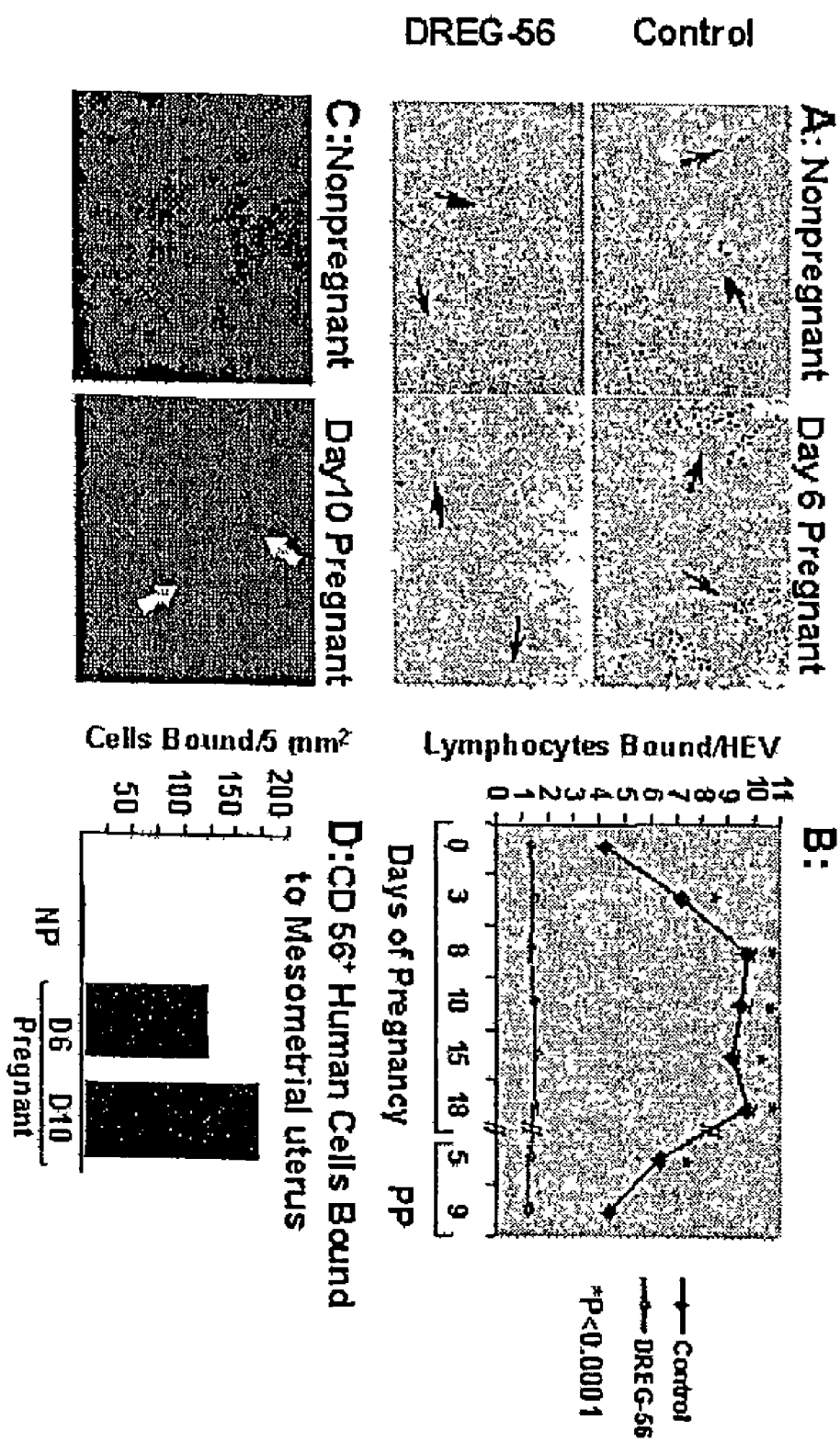
FIG. 2 is a schematic showing time course studies of human peripheral blood lymphocytes (PBL) bound per high endothelial venule (HEV) of peripheral lymph nodes (PLN; top panel), of Peyer's patches (PP; middle panel), and endothelial cells of small blood vessels of pancreas (bottom panel) over pregnancy and postpartum periods of the mouse tissue donor. The depicted figures represent data from one experiment using the same PBL and same tissue donors. Similar outcomes were obtained in replicate (n=3) experiments that examined the full gestational timecourse with peak adherence detected between gd 6 and 8. Datapoints represent the mean number±SD of lymphocytes bound/vessel and are based on triplicate counting of 300–500 HEV or small vessels.

C57Bl/6J (Jackson Laboratory, Bar Harbor, Me.) and Balb/c (Taconic, Germantown, N.Y.) mice, aged 7–8 wk were studied. Some females were used for timed matings with the morning of the copulation plug designated gd 0. Other females (n=34) were surgically ovariectomized under Avertin anaesthesia (24). Females were rested 6 days and then received daily subcutaneous injections of either hormone dissolved in sesame oil or sesame oil alone between 9.00–11.00 a.m. as indicated in FIG. 2.[81-84] Some of the Ovx hormone-treated mice also had 10 μl sterile sesame oil injected into a uterine horn to induce decidualization 48 h prior to euthanasia. Ovx mice were euthanized 24 hours after receiving their last injection and vaginal smears were collected and stained with Wright-Giemsa to confirm treatment success. Non-pregnant (NP) controls were virgin females who had never been paired with males. All procedures were performed under appropriate animal utilization protocols.

The following samples were collected from each mouse and embedded in OCT (Miles Laboratories) for cryosectioning: i) a pool of 10–12 PLN from subcutaneous and intermuscular sites; ii) a pool of 10–12 intestinal PP; iii) the entire pancreas; and iv) the uterus. For some experiments, the median iliac lymph nodes that drain the pelvic organs, including the uterus, were also dissected. Non-decidualized uteri were trimmed at the ovarian and cervical ends, then incised longitudinally along one side on an axis midway between the mesometrial and anti-mesometrial aspects. The mesometrium (the mesentery suspending the uterus, also known as the broad ligament) was not removed and served as a positional landmark during analyses. For embedding, samples were oriented to produce full thickness longitudinal sections that included both antimesometrial and mesometrial sides. Uteri from gd 3 were flushed for blastocysts to confirm pregnancy.

Assay of Functional Cell Adhesion Under Shear to Frozen Tissue Sections

The cell suspensions evaluated for adhesive interactions with endothelium were human peripheral blood lymphocytes (PBL) isolated from random (female and male) normal donor buffy coat leukocyte concentrates (American Red Cross, Rochester, N.Y.);[85,68] and TK-1 cells (an alpha integrin$^{high}$, L-selectin$^{low}$ mouse T lymphoma cell line).[85] In selected experiments, human PBL were cultured 6 hr at 37° C. or 40° C. before being applied to tissue sections, as previously described[12]. In all assays, some cell aliquots were incubated with function blocking mAb specific for human L-selectin (DREG-56, American Type Cell Collection [ATCC], Manassas, Va., 10 μg/ml) or human alpha4 integrin (HP2/1, Coulter Immunology, Hialeah, Fla., 10 μg/ml). To identify adherent human NK cells, PBL aliquots were pre-labeled with anti-CD56 mAb (NKG1, Coulter Immunology, diluted 1:100) followed by rabbit anti-mouse Ig-rhodamine isothiocynate (RITC) Ab as described previously (10;29). Control aliquots were treated with the secondary reagent alone. Lymphocytes were overlaid on 12 μm cryosections of murine tissues and rotated (112 rpm for PBL and splenocytes, 95 rpm for TK-1 cells) at 4° C. for 30 min. In some instances, tissue cryosections were pre-treated with MECA-367 a mAb to MAdCAM-1 (ATCC, 1:4 dilution of hybridoma conditioned medium). Following removal of non adherent cells, glutaraldehyde-fixed specimens were stained with 0.5% toluidine blue and adhesion was scored on 300–500 HEV/PLN or PP specimen or equivalent numbers of small vessels in pancreatic tissue. When CD56-pre-labeled cells were used, fluorescent cells were quantified in 10 high power fields (HPF; one HPF=5 mm$^2$) at 200× magnification using an Olympus BH2/RFL fluorescence microscope (Olympus Optical, Tokyo, Japan) (10;29). All enumerations were done thrice.

Results (a) Pregnancy Promotes Organ-Specific Adhesive Function in Endothelial Cells To evaluate the effects of pregnancy on endothelial cell interactions in peripheral organs, adhesion of human PBL to endothelium was assessed in PLN, PP, and pancreas from virgin, pregnant and postpartum mice (FIG. 3). Onset of pregnancy, prior to blastocyst implantation (gd 3), significantly elevated adhesion to HEV in PLN above that of PLN from virgin mice (p<0.05). Peak levels of adhesion were achieved early post implantation (gd 6–8). An equivalent gain in adhesion was demonstrated at gd 6 in LN that provide pelvic organ drainage (not shown). Adherent cells were uniformly small in size, 6.8±0.4 μm. Once peak levels of adhesion were achieved, these levels were sustained throughout the remainder of gestation (i.e. to gd 18 with birth at gd 19). In PLN of mice taken 5 and 9 days postpartum (times selected to represent completion of the first and second postpartum estrous cycles), adhesion of PBL dropped to levels found in PLN from virgin mice. Pregnancy-induced adhesion of PBL to HEV in PLN was L-selectin-dependent, as shown using an L-selectin function blocking mAb (p<0.001, FIG. 3, top panel).

Pregnancy also increased lymphocyte adhesion to HEV in PP. However, in contrast to LN HEV, adhesion in PP HEV adhesion declined to baseline during late pregnancy (FIG. 3, middle panel). Adhesion to PP HEV was blocked by MECA367, a mAb that functionally inhibits both L-selectin and alpha integrin-mediated binding to MAdCAM-1 (FIG. 3, middle panel). In sharp contrast to the gains in lymphocyte-endothelial cell adhesion detected in HEV of LN and PP, adhesion was not altered in the non-differentiated squamous endothelium lining small vessels of the pancreas at any gestational time point (FIG. 3, lowest panel). These data suggest that only a restricted subset of vessels is targeted by pregnancy-driven signals for lymphocyte egress.

(b) Increased Adhesion of Lymphocytes to HEV is Induced by Ovarian Steroid Hormones Receptors for E and P4 are expressed by endothelial cells and may contribute to the observed pregnancy-induced changes in lymphocyte-endothelial cell interactions. To address these potential mechanisms, Ovx mice were studied using hormone replacement strategies. Ovx mice were pre-treated with physiologic (100 ng)[81] or therapeutic (1 μg)[84] doses of E2 (called low and high), with P4,[81,82] or with combined low dose E2 plus P4. In addition, because decidualization is an important feature of mouse implantation and not induced by hormone treatment alone, additional E2+P4-treated Ovx animals were studied in which decidualization was induced artificially by injection of sesame oil into a uterine horn.[81,82] All hormone treatments promoted statistically significant gains in L-selectin-dependent adhesion of human PBL indicator cells to PLN HEV as compared to the basal levels of adhesion observed in either placebo-treated (oil) or virgin control mice (FIG. 3A). The murine TK-1 indicator cell line ($\alpha_4\beta_7$ integrin$^{high}$, L-selectin$^{low}$) was used to identify the effects of hormone treatment on alpha4 integrin/MAdCAM-1-dependent adhesion events in PP HEV. All hormone conditions significantly elevated TK-1 cell adhesion to PP HEV through a mechanism that could be blocked by the $\alpha_4\beta_7$ integrin-specific DATK-32 mAb (FIG. 3B). Induction of decidua did not promote adhesion in PLN or PP HEV above that induced by hormone treatment alone (FIG. 3A, B). The functional levels of adhesive changes stimulated by E2 treatment of Ovx mice were similar to the peak levels stimulated by pregnancy in HEV of secondary lymphoid organs (therapeutic E2 dose compared to gd 10 in FIG. 3C, D). As shown in FIG. 3E and F, administration of E2 had no effect on adhesion of PBL or TK1 cells to pancreas.

(c) Increased Adhesion of Lymphocytes to Endometrium is Promoted by E2 and P4

To assess steroid hormone-mediated effects on adhesiveness of endometrium for NK cells, CD56-labeled human PBL were applied to uteri from Ovx mice treated with oil, E2 (low or high dose), P4 or E2+P4 with or without decidualization. Adhesion was assessed under mechanical shear. All hormone treatments promoted similar levels of statistically significant adhesion compared to adhesion on control uterine tissue (placebo-treated Ovx or virgin; FIG. 4). The presence of decidualized stroma had no independent effect. Adhering CD56$^{bright}$ cells were randomly distributed across all of these uteri as single cells. The adherent CD56$^{bright}$ cells were heterogeneous in size, some being larger cells (8.01–9.01 μm as compared to 6.8±0.41 μm). Adhesion was blocked using either DREG56 or HP2/1 mAbs to L-selectin and alpha4 integrin, respectively (FIG. 4).

A high proportion of adherent cells in both naturally pregnant uteri at gd 6 and in hormone-treated Ovx uteri were CD56$^{bright}$ (FIG. 5). This represented a significant enrichment in this NK cell phenotype since less than 2% of lymphocytes in the original overlays were CD56$^{bright}$. Furthermore, numerous clusters of large CD56$^{bright}$ cells were noted on the gd 6 uteri but not on hormone-treated uteri. Cells in these clusters could not be quantified reproducibly and were excluded from the enumeration. The values presented for pregnant uteri therefore underestimate the actual numbers of cells bound under pregnancy conditions. Further evaluations were performed using unlabeled human PBL, stained with toluidine blue for scoring under light microscopy. This provided better visualization of adhering cells and clusters and improved details of anatomic localization. As shown in FIG. 6 prior to decidualization (virgin and gd 3), adherent cells were randomly distributed both mesometrially and anti-mesometrially and bound as single cells. In sharp contrast, using the same cell suspension within the same experiment, decidualized gd 6 uteri bound some of the lymphocytes in small clusters. The number of bound lymphocytes/cluster was markedly increased on gd 10 uteri. Both single cells and clusters preferentially adhered to DB. In parallel experiments using CD56-pre-labeled cells, the clusters were shown to be mixtures of both $CD56^{bright}$ and $CD56^{dim}$ cells. These clusters of adherent cells were not observed in uteri from hormone-treated mice or in peripheral tissues of any of the mice investigated.

Discussion

The exquisite microdomain compartmentalization of the decidualized mouse uterus of early pregnancy is due to the transient development of highly differentiated vessels expressing known vascular adhesion molecules in non-overlapping patterns.[40,86] The biological function of this compartmentalization is postulated to be recruitment and localization of specialized, distinct leukocyte subsets. Precursors for the dominant lymphocyte subset of early pregnancy, the uNK cells, do not self renew in the uterus but are recruited during the first trimester.[87,88] Transplantable uNK precursor cells have been found in BM, neonatal and adult thymus, spleen, LN and liver with PLN and spleens from pregnant donors being the richest sources.[87,88] For pre-uNK or uNK cells to leave the circulation and move into the uterus, interactions with endothelial cells are required. It was observed that a pregnancy-induced gain in adhesive function of HEV using human PBL as indicator lymphocytes in adhesion assays conducted under shear forces and PLN from gd 6 and virgin mice as tissue substrates.[87,88] Because of the potential biological relevance of this observation to lymphocyte homing into the pregnant uterus, which appears to be important for antigen monitoring, for promotion of pregnancy-dependent physiological changes to the endometrium and its vasculature[27] and to lymphoid organ hypertrophy and involution during pregnancy,[36,37,89] an extended study was undertaken.

Pregnancy-induced gains in endothelial cell adhesive properties were found in selected tissues including uterus and secondary lymphoid tissues (LN, PP). Notably, these changes in adhesion were highly tissue specific as evidenced by the failure of pancreatic endothelium to respond to the pregnant state. Consistent with the notion that these changes were mediated by the ovarian steroids, E2 and P4, it was observed that treatment of Ovx mice with either steroid fully mimicked the functional gains in adhesion promoted by pregnancy in secondary lymphoid tissues. Hormonally-induced changes in adhesion at LN and PP sites were mediated by L-selectin and $\alpha_4\beta_7$ integrin respectively, consistent with known roles of these molecules in trafficking to these secondary lymphoid tissues.[62,68,85,87] Thus, it is unlikely that new adhesion pathways are induced by pregnancy. More probably, novel regulatory events are being detected. Since it has been demonstrated that E2 stimulation of human vascular endothelial cells (HUVEC) results in increased expression of the adhesion molecule ICAM-1 (21), and stabilization of mRNA for adhesion molecules ICAM-1, V-CAM, and E-selectin, it is possible that ligands for L-selectin (PNAd) and $\alpha_4\beta_7$ (MAdCAM) are similarly influenced by hormonal stimulation, although that has not been reported to date. VCAM-1 has been found to be the most dramatically upregulated endothelial cell adhesion molecule in mouse DB,[86] but PECAM-1 and alpha4 integrin were strongly upregulated on human uterine myometrial endothelium when cells were cultured with E2 and P4.[90]

Movement of lymphocytes including uNK cells and/or their precursors between secondary lymphoid organs into the uterus would involve transit across two endothelial surfaces, that in a lymphoid tissue and that in the uterus. Therefore, steroid hormone-mediated effects on uterine promotion of $CD56^{bright}$ cell binding were investigated using Ovx mice in which hormone levels were controlled. Endometrium from Ovx-placebo treated mice could not be distinguished functionally from that of virgin females. Both bound mixtures of $CD56^{bright}$ and $CD56^{dim}$ cells at low frequency across all of the endometrial stroma. In both types of tissue, occasional larger cells bound, some of which were $CD56^{bright}$, as previously reported for virgin and pregnant uteri.[87,88] Gain in uterine adhesiveness was induced by all steroid hormone treatments. Unexpectedly, equivalent functional changes were induced in uterine tissue by both physiological[81] and pharmacological[84] doses of E2, by E2 compared to P4[83] and by E2+P4.[82,83] Quite surprisingly, artificial induction of endometrial stroma cell decidualization[83] did not modify the levels of adhesion beyond that seen following administration of hormones only. While not wishing to be limited by theory, this may suggest that maximal functional changes had been induced using single agents and points to redundancy in the mechanisms used by the pregnant uterus to promote homing of specific lymphocyte subsets. Blocking studies again indicated that known adhesion pathways[62] were being promoted by the steroid hormones. Administration of E2 or P4 to mice increases glycotransferase and sialyltransferase activities in the uterus.[91] Notably, these enzymes are known to modify L-selectin ligands.[92] Alpha fucotransferase and NAC-glucosamine-6-0-sulfotransferase expression in the MLAp of gd 6 and 10 B6 mice have also been identified in a cDNA microarray analysis (unpublished).

Although artificially-induced decidua in normal mice lacks compartmentalization, these tissues are able to recruit uNK cells. Lymphocytes adhering to artificially induced decidua were always dispersed and never found as aggregates. The decidualized, pregnant uterus induced an aggregating/clustering behavior in the viable adherent cells that was microdomain restricted (FIG. 6). This suggests that recruitment is distinct from localization. Recruitment appears to be hormone mediated while localization appears to be hormone independent, but requires lymphocyte recognition of fetal trophoblast. Broadly, these data define limits in the widely used model of deciduomata induction in rodents and demonstrate that this model is not fully representative of decidua induced by blastocyst implantation.

Example 3

Goals of Example 3 were i) to assess the role of pregnancy and/or pregnancy hormones on the adhesive properties of mouse splenocytes and ii) to determine the role of the adhesion molecule L-selectin in mediating adhesion.

Materials and Methods

Mice and Tissue Dissections

C57BI/6J (Jackson Laboratory, Bar Harbor, Me.) and C57BI/6 mice genetically altered to lack a functional L-selectin adhesion molecule (L-selectin$^{-/-}$), aged 7–8 wk were studied. Some females from both strains of mice were used for timed matings with the morning of the copulation plug designated gd 0. Non-pregnant (NP) controls were virgin females who had never been paired with males. Other C57Bl/6J females (n=34) were surgically ovariectomized under Avertin anaesthesia[24], rested 6 days and then received daily subcutaneous injections of either hormone dissolved in sesame oil or sesame oil alone between 9.00–11.00 a.m. as indicated in FIG. 2.[81-84] Some of the Ovx hormone-treated mice also had 10 µl sterile sesame oil injected into a uterine horn to induce decidualization 48 h prior to euthanasia. Ovx mice were euthanized 24 hours after receiving their last injection and vaginal smears were collected and stained with Wright-Giemsa to confirm treatment success. All procedures were performed under appropriate animal utilization protocols.

Assay of Functional Cell Adhesion Under Shear to Frozen Tissue Sections

In all assays, some cell aliquots were incubated with function blocking mAb specific for mouse L-selectin (MEL-14, ATCC, hybridoma conditioned medium diluted to 1:4), or mouse $\alpha_4\beta_7$ integrin (DATK-32, Coulter Immunology, 10 µg/ml). Lymphocytes were overlaid on 12 µm cryosections of PLN from virgin mice and rotated at 112 rpm at 4° C. for 30 min. In some instances, tissue cryosections were pre-treated with MECA-367 a mAb to MAdCAM-1 (ATCC, 1:4 dilution of hybridoma conditioned medium). Following removal of non-adherent cells, glutaraldehyde-fixed specimens were stained with 0.5% toluidine blue and adhesion was scored on 300–500 HEV/PLN. All enumerations were done thrice.

Role of L-Selectin in Mediating Adhesion

In the experiments investigating the role of L-selectin in mediating adhesion between splenocytes and PLN, splenocytes from C57BL/6J mice and L-selectin$^{-/-}$ mice were pre-labelled with either CellTracker green CMFDA (5-chloromethylfluorescein diacetate) or CellTracker blue CMAC (7-amino-4-chloromethylcoumarin) (Molecular Probes) and mixed in a 1:1 ratio prior to use in the adhesion assay. To assess the effect of the dye in the adhesion assay, dyes were reversed in a second experiment and unlabelled cells were mixed in place of control cells in a third experiment. Fluorescent cells were quantified in 10 high power fields (HPF; one HPF=5 mm$^2$) at 200× magnification using an Olympus BH2/RFL fluorescence microscope (Olympus Optical, Tokyo, Japan). All enumerations were done thrice.

Results a) Pregnancy and Steroid Treatment Enhances Adhesion of Splenocytes to PLN Having established that both pregnancy and pregnancy-associated hormones stimulate endothelial cell adhesion, the functional analysis of these physiologic mediators was extended to lymphocytes. Splenocytes from all groups of Ovx mice (FIG. 2) were assessed for L-selectin-dependent adhesion to HEV of PLN from virgin mice. As shown in FIG. 7A, all steroid hormone treatments enhanced L-selectin-dependent adhesion of splenic lymphocytes under shear compared to levels in the placebo treatment group. Moreover, these increases in L-selectin binding function were comparable to those induced by pregnancy as well as to those induced by in vitro lymphocyte stimulation using fever-range temperature (FIG. 7B). Adhesion induced in this assay by fever range hyperthermia was previously equated to a 4–5 fold increase in lymphocyte homing potential in vivo.[85]

b) L-Selectin has an Important, but not Solitary Role in Mediating Enhanced Adhesion During Pregnancy In FIG. 8, the results of the L-selectin experiment are summarized. Each experiment gave identical results, regardless of which CellTracker dye was used. This demonstrates that the effects of pregnancy are cumulative; lowest adhesion is observed when splenocytes from a virgin donor are applied to tissue from a virgin donor. Adhesion to virgin tissue is enhanced when the donor lymphocytes come from a pregnant animal, further increased when the tissue source is from a pregnant animal and maximized when both cells and tissue come from pregnant animals.

Using cells from the C57BL/6J mice, adhesion is consistently higher on the same tissue samples than cells from the L-selectin$^{-/-}$ mice. Lack of the L-selectin molecule results in the same pattern of adhesion as is observed in the B6 mice, with significant increases on pregnant tissue, but this level of adhesion is approximately ⅔ that of the B6 mice.

Discussion

Pregnancy and its associated hormones alter not only the vascular endothelium to enhance cell trafficking but also the ability of lymphocytes (splenocytes) to recognize and adhere to molecules expressed on vascular endothelium. This recognition appears to be mediated in part, but not exclusively, by L-selectin, a molecule highly expressed on the surface of CD56$^{bright}$ natural killer cells. Previous work also implicates roles for α4 integrin and LFA-1 in establishing firm adhesion between lymphocytes and endothelium in the pregnant uterus[39, 40].

The coordinated effects of pregnancy on endothelium, on lymphocytes and on their interactions are reminiscent of findings in other models of normal physiological change such as inflammation and fever. Amplification of lymphocyte/endothelial interactions in specialized HEV of selected tissue sites (LN, PP) while sparing non-lymphoid tissues, has been proposed to focus immune response to these sites, thus preventing an unproductive exodus to less relevant sites. Defining the steroid regulated pathways for lymphocyte recruitment to the uterus has potential therapeutic importance for promoting lymphocyte localization to uteri of patients at risk for implantation failure or pre-eclampsia and to non uterine tissues in patients with other hormone-sensitive diseases such as some tumours and endometriosis. Such information may also help to explain inefficiencies in combination therapies that involve steroid hormone replacement.

Example 4

Effect of Hormones on Human Lymphocytes

Goals of example 4 were to i) determine the effect of the menstrual cycle on the recognition of human peripheral blood lymphocytes (PBL) of adhesion molecules expressed on PLN and PP from virgin and pregnant mice and to ii) correlate the hormones involved in cycle regulation to adhesion of human PBL to mouse uterine tissue.

Materials and Methods

Mice and Tissue Dissections

C57Bl/6J (Jackson Laboratory, Bar Harbor, Me.) aged 7–8 wk were used for timed matings with the morning of the copulation plug designated gd 0. Non pregnant (NP) controls were virgin females who had never been paired with males. All procedures were performed under approved animal utilization protocols. A pool of 10–12 PLN from subcutaneous and intermuscular sites were collected from each mouse and embedded in OCT (Miles Laboratories) for cryosectioning. Non-decidualized uteri were trimmed at the ovarian and cervical ends, then incised longitudinally along one side on an axis midway between the mesometrial and anti-mesometrial aspects. Implantation sites from pregnant uteri were trimmed and cut horizontally mid-way through the site and placed cut face down into biopsy cryomolds and flash frozen.

Human Subjects and Blood Sampling

Male and female subjects of legal age and in good health were recruited to donate up to 30 ml of blood, using venipuncture into evacuated, sterile blood collection tubes. All subjects were informed about the risks of participation in this study and signed approved informed consent forms. The blood was layered onto an equal volume of Histopaque 1.077 (Sigma) and centrifuged at 400×g for 30 min at RT according to manufacturers instructions. The cells at the interface were collected, washed thrice and counted.

Preliminary experiments were done to determine the lowest number of cells possible to detect significant differences in lymphocyte adhesion. Replicate experiments using $10^7$, $5 \times 10^6$, $2.5 \times 10^6$, and $10^6$ cells per 100 µl from several donors (4) were applied to LN from both virgin and pregnant animals in a standard adhesion assay. After washing, fixing and staining, adherent cells were counted.

The effects of anti-coagulants on adhesive properties of isolated PBL were assessed. Ten ml of blood was collected by venipuncture (40 ml collected per subject) into sterile evacuated tubes containing either Acid Citrate Dextrose (ACD), EDTA, Sodium Citrate, or heparin. Lymphocytes were isolated as described above and applied to sections of LN from pregnant mice. The sections were assessed for lymphocyte adhesion by microscopy.

It has been previously demonstrated that fever range temperature resulted in enhanced adhesion of PBL. To determine the effect of refrigeration on the adhesive properties of PBL, four samples of blood from each of four different subjects were incubated at 20° C. for 4 h, at 37° C. for 4 h, at 4° C. for 4 h or at 4° C. for 3.5 h, then warmedback to 37° C. for 30 min. Then lymphocytes were isolated as described above and cells were used in an adhesion assay. Lymphocytes from freshly drawn blood were used as a control.

Effects of the Menstrual Cycle on Lymphocyte Adhesiveness

Seven women of legal and reproductive age, not using hormonal birth control and giving informed consent, were recruited to donate blood at 12 timepoints of their menstrual cycle. They were asked to maintain a record of their temperature throughout one cycle using a basal body thermometer and they started donating blood at a random timepoint of their cycle. Twenty five ml of blood were drawn thrice weekly for 4 weeks. White blood cells were isolated and $2.5 \times 10^6$ cells were overlaid onto tissue section of PP and LN from virgin and pregnant (d8) mice. Function-blocking antibodies to L-selectin or alpha-4 integrin were used and found to significantly reduce adhesion. Two hundred HEV were counted per slide and were scored blind encoded. After the completion of counting, volunteers submitted their temperature charts and the results were correlated with the phase of the cycle as indicated by first day of menses and with temperature shift (indicating that ovulation had occurred). Significant differences were detected using ANOVA.

The second group of seven subjects also kept basal body temperature charts throughout their cycle, but in addition, commenced use of a commercial LH detection kit (Clearplan) on day 11 of their cycle. Blood was collected by venipuncture on day 8, day of LH surge and day 22 of their cycle. Serum was collected at each of these timepoints and assayed by ELISA for concentration of estradiol ($E_2$) (DRG Instruments, Germany), luteinizing hormone (LH) (Biocheck, Inc. Burlingame, Calif.) and progesterone ($P_4$) (Biocheck, Inc. Burlingame, Calif.).

Results

Dose Response

Due to the limited number of PBL available from 25 ml of blood, a dose response curve of the number of cells used per tissue section was done. In FIG. 9, the results of 3 independent experiments are shown. From this, it was determined that the minimum number of cells that could be used while maintaining the ability to detect a significant increase in adhesion in comparison to a control was $2.5 \times 10^6$ cells.

Effect of Anti-Coagulants on Adhesive Properties of Lymphocytes

Next, the possible effect of the anti-coagulant used to collect the blood on the adhesive properties of the isolated lymphocytes was investigated. Four commonly were used anti-coagulants on 3 subjects each. The results of those experiments are summarized in FIG. 10. The cells isolated from blood containing acid citrate dextrose (ACD) demonstrated superior adhesion than those isolated from EDTA or heparin. The sodium citrate did not interfere with adhesion, but the numbers of lymphocytes isolated from these samples was consistently lower than with the other anti-coagulants. Therefore, ACD was selected as the anti-coagulant for future experiments.

Effect of Temperature of Blood on Adhesive Properties of Lymphocytes

The results of the temperature assay are shown in FIG. 11. Freshly isolated human lymphocytes (first bar) were used as a reference value. Warming the blood to 37° C. results in an increase in adhesive ability, significantly higher than the control (freshly isolated lymphocytes), while storage at room temperature has no effect on adhesion. It was demonstrated that chilling blood significantly reduces the ability of the isolated human lymphocytes to recognize and bind to ligands expressed on mouse tissue. Chilled blood, which is then re-warmed to 37° C. demonstrates a rebound in adhesion, but not to levels seen in either the control or the 37° C. cells.

Effect of the Menstrual Cycle on Adhesive Properties of Lymphocytes

As shown in FIG. 12A, there was no significant difference in lymphocyte adhesion to LN from virgin mice at any stage of the menstrual cycle. However, we found that lymphocytes taken at the peri-ovulatory period adhered at a significantly higher level than those from the proliferative or luteal phase of the menstrual cycle in an L-selectin dependent manner in LN from a pregnant animal (FIG. 12B). The same pattern of adhesion was evident in PP from both virgin and pregnant animals (FIG. 12C and D). Adhesion to PP was shown to be alpha 4 integrin dependent.

In FIG. 13, the results of the second experiment are shown. Here blood samples were taken at only 3 timepoints and applied to LN and uteri from pregnant mice only. In panel A, the same pattern of increased adhesion to LN is seen in the periovulatory period as was demonstrated in FIG.

13. Panel B shows that the effect at the LH surge is greater on uterine tissue than was seen on LN.

Discussion

During the latter half of the menstrual cycle, a subset of Natural Killer (NK) cells expressing the phenotype $CD56^{bright}$, $CD16^{dim}$ home to the uterus. These cells constitute the most abundant uterine lymphocyte population during early to mid-pregnancy. It has been previously shown that in mouse tissue (uterus, lymph node and Peyer's Patches), pregnancy, as well as exposure to the pregnancy hormones 17β-estradiol ($E_2$) or progesterone ($P_4$), markedly up-regulated both L-selectin and $α_4$-integrin-dependent adhesion of human CD56 expressing cells. Similarly, adhesion of splenocytes from pregnant or hormone treated animals to LN from virgin mice was significantly increased over virgin or sham-treated controls. Here, these studies have been extended using peripheral blood lymphocytes (PBL) from healthy, female volunteers of reproductive age for a time-based study of the effects of the menstrual cycle on the adhesive properties of PBL to mouse tissues. It was found that adhesion of human PBL to pregnant mouse LN, PP and uterus peaked at mid-cycle, in the peri-ovulatory period. Peak adhesion was observed on the day of LH surge, as determined by a commercial LH detection method. LH, E2 and P4 levels were confirmed by ELISA.

The primary differences between the previous experiments and these experiments is that lymphocytes were immediately prepared and assessed for adhesion on PLN from virgin or day 7 pregnant mice and on Peyer's Patches (PP) from the same donors within 3 hours of drawing blood. The central question for the research program is how to monitor changes in human lymphocytes modified by pituitary or steroid hormones, in their interactions with endothelium. It was anticipated that changes which would promote movement of the lymphocytes from the circulation into the uterus during pre-decidualization (LH+3–5) and that would be sustained during early pregnancy. The data confirm that PBL exhibit higher affinity for adhesion molecules expressed on vascular endothelium in the peri-ovulation phase, indicating that either peak E2 or LH itself, may trigger NK cells to traffic to the uterus. The adhesion assay only measures the first 2 steps of the homing process. It has been determined that lymphocytes are slowed and arrested, not that they exit the blood.

The chemokine receptor repertoire reported for $CD56^{bright}$ cells may contribute to homing of this lymphocyte subset to discreet regions of the uterus. The uNK cells belong to the $CD16^-CD3^-CD56^{bright}$ subset of NK cells and express high levels of L-selectin.[5,102,103] This subset also expressed high levels of CCR5, CCR7, CXCR3 and CXCR4 and low levels of CX3CR1.[102] In migration assays, $CD16^-CD3^-CD56^{bright}$ NK cells were differentially enriched by responding to RANTES, I-TAC and IP10 with lower enrichment in response to MCP-3. In dose response migration assays, the most dramatic responses were to the CCR7 ligands MIP-3β, and SLC and to the CXCR3 ligands I-TAC and IP10.

Examples 5 and 6

These examples aim to define the normal, hormonally- and gestationally-induced changes in adhesion properties of women's lymphocytes with endothelial cells that recruit NK cells into the decidualizing uterus for promotion of successful decidualization, implantation, uterine artery modification and pregnancy.

Materials and Methods

Human Subjects and Blood Sampling

The study requires 2 groups of women who have given informed consent and whose ovulation cycles are defined by monitoring of blood estradiol and LH levels. All donors will be prescreened HIV- and Hepatitis-free. Example 5 requires serial blood sampling of n=30–35 patients across a normal luteal phase of the cycle and into early pregnancy (to day 40). Patients (n=30–35) enrolled in a REI program anticipating transfer of banked frozen embryos will be recruited. Each woman will give an additional 20 ml blood at regularly scheduled endocrine monitoring bleeds (cycle days 10, 12, 14, 16), at the day of transfer and on days 18 and 40 after transfer, respective times for pregnancy diagnosis endocrinologically and by ultrasound. Bleeding will be conducted and hormone values measured will become available, as blind encoded data. Example 6 requires serial blood sampling during COH and into early pregnancy (day 40). Patients (n=20) will again be recruited from a REI program at UWO and monitored serially as in Example 4. Six or 7 serial collections are anticipated per patient and each will be encoded and couriered for immediate analysis. Patient exclusion criteria include lack of 2 good to high quality embryos, and age over 39. Differences in conception rates in the patient groups are currently attributed to cryogenic embryo damage. Historical conception rate data will be available for statistical comparisons.

Mice:

C57Bl/6J mice will be purchased from Jackson Laboratories and maintained for breeding. Non-pregnant and gd 7 will be used. All pregnancy time points required in a single experiment must be available on the same day. Mice will be euthanised, uterus, and LN dissected and placed in OCT compound for immediate freezing in $N_2$ chilled isopentane and storage. Adhesion molecule stability is 10 days. On assay days, 12 μm cryostat sections will be cut from selected test tissues and melted onto glass coverslips.

Quantitative Frozen Tissue Adhesion Assay Under Shear:

Lymphocytes will be prepared by Histopaque 1.077 (Sigma) centrifugation and adherent cell depleted using established protocols.[5,66,68] $5×10^6$ cells are routinely used per section; $2×10^6$ are adequate. In all experiments, some lymphocytes will be pre-incubated 30 min at 20° C. with MAb (such as DREG-56, an anti-L-selectin function blocking Ab or T51/22, an LFA-1 blocking Ab, both from ATCC, anti-hu alpha4 integrin (Immunotech) anti CD56-PE (PharMingen), anti-CD3-FITC (Becton Dickenson) or isotype matched control antibodies before being applied to tissue sections in a 100 μl volume of RPMI medium +10% bovine serum. In other instances, tissue sections will be pre-incubated 30 min at 4° C. with antibodies directed against PNAd (MECA-79), MAdCAM-1 (MECA-367), VCAM-1 (MK2.7), I-CAM-1 (YN1/1.7) or species appropriate isotype negative control reagents, prior to initiation of adhesion. These antibodies are on hand as hybridomas from ATCC. Antibody dilutions will be determined by prior studies in Dr. Evan's laboratory. In a cold room, adhesion assays are conducted under shear[68,70] and then washed, fixed and stained. 300–500 high endothelial venules are scored 3 times in lymphoid tissues to obtain a mean binding of lymphocytes/HEV. For uterine tissue, vessel associated cells are countered per 10 high power fields and tissue adherent cells/mm² in different decidual regions as gestationally appropriate. To provide an internal control for standardization of comparisons between experiments, the murine B cell line 300.19, transfected with and expressing full length human L-selectin[67,106] will be used in each adhesion assay as the positive control. Some unblocked completed assay slides will be post immunostained to evaluate IFN-γ (antibody from Becton-Dickenson) in adhering cells.

Estradiol and LH Assays:

ELISA will be used to quantify estradiol and LH in plasma from leukophoresis donors and patients.

Statistics: Mean values between paired groups are compared using Student's T test. ANOVA is used for multiple group comparisons. Statistical procedures will be optimized to correlate adhesion and endocrine data with pregnancy outcomes.

Example 5

To Quantify Changes in Lymphocyte/Endothelial Cell Interactions Associated with Transition from the Luteal Phase to Pregnancy:

Assays will be conducted serially on lymphocytes provided by patient volunteer recipients of frozen embryos until 5 gd 40 pregnancies have been monitored. Uterine sections will be non pregnant and a constant pregnancy day. Inbred mice must be used to maximally reduce variation in the uterine tissues. This example will characterize the stability or dynamics of lymphocyte/endothelial cell interactions within individuals during the late luteal phase of uterine decidualization and during establishment of pregnancy.

Example 6

To Monitor the Effect of COH on Lymphocyte/Endothelial Cell Interactions:

Assays will be conducted serially on lymphocytes provided by patient volunteer recipients of fresh embryos following COH until 5 gd 40 pregnancies have been monitored. Adhesion assays will be identical to those in Example 5 and patients will be run concurrently as available. This example will reveal the way a standard IVF hormone therapy protocol[107] modifies interactions between lymphocytes and uterine tissue by comparing the results to those from Example 5. The information gained will be used to to reassess ovulation protocols or to modify hormone therapy for other types of patients. The experimental design also permits correlations of changes in adhesive functions to circulating hormone levels.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated in its entirety.

TABLE 1

Results of uterine segment transplantation

| Donor →Host | Animal Identity number | # of fetuses in graft:host segments | Grafter horn maternal tissues in graft | density of uNK cells at graft sites* | Non-grafted Horn #. of fetuses |
|---|---|---|---|---|---|
| CD1 →CD1[†] | 1 | 1:3 | MLAp[‡], DB[§] | +++ | 0 |
|  | 2 | 0:0 | deciduoma | + | 7 |
| CD1 →CD1[¶] | 3 | 1:1 | MLAp, DB | +++ | 4 |
|  | 4 | 1:3 | MLAp, DB | +++ | 6 |
| CD1 →tgε26 | 5 | 0:0 | deciduoma | − | 6 |
|  | 6 | 0:0 | deciduoma | − | 1 |
|  | 7 | 0:1 | deciduoma | − | 3 |
|  | 8 | 0:0 | normal uterus | − | 0 |
| SCID →tgε26 | 9 | 0:0 | deciduoma | − | 5 |
|  | 10 | 0:0 | normal uterus | − | — |
|  | 11 | 0:0 | deciduomata | − | 1 |

+++ = more than 50 uNK cells/mm², 
+ = 5 or fewer uNK cells/mm², 
− = no uNK cells 
[†]autografted, non grafted horn was re-anastomosed 
[‡]MLAp, mesometrial lymphoid aggregate of pregnancy 
[§]DB, decidua basalis 
[¶]donor and recipient were different CD1 mice

TABLE 2

Mean density of uNK cells/mm$^2$ on gd 10 in mesometrial tissues of NK/uNK cell deficient mice transplanted on gd 0 and controls

| Genotype | Graft | Cells inoculated/ recipient × 10$^7$ | Dams/ fetuses | Means Cells/mm$^2$ ± SD) | |
|---|---|---|---|---|---|
| | | | | DB | MT |
| Control | | | | | |
| tgε26 | PBS | — | 3/9 | 0 | 0 |
| RAG-2$^{-/-}$/γc$^{-/-}$ | PBS | — | 3/9 | 0 | 0 |
| SCID | PBS | — | 2/8 | 48.5 ± 14.3 | 129.1 ± 26.0 |
| B6 | PBS | — | 2/4 | 26.5 ± 3.3 | 74.7 ± 4.8 |
| F1 | PBS | — | 1/3 | 53.3 ± 8.3 | 72.1 ± 5.1 |
| Transplanted | | | | | |
| RAG-2$^{-/-}$/γc$^{-/-}$ | NP B6 adult thymus | Na | 2/6 | 1.6 ± 2.2* | 0.6 ± 1.3* |
| RAG-2$^{-/-}$/γc$^{-/-}$ | gd3 B6 thymus | na | 2/6 | 2.5 ± 1.1* | 5.2 ± 2.7* |
| RAG-2$^{-/-}$/γc$^{-/-}$ | gd5 B6 thymus | na | 3/9 | 9.6 ± 5.2* | 7.0 ± 5.0* |
| RAG-2$^{-/-}$/γc$^{-/-}$ | Neonatal B6 thymus | na | 2/6 | 1.7 ± 0.8* | 3.7 ± 1.0* |
| RAG-2$^{-/-}$/γc$^{-/-}$ | NP adult SCID liver | 0.1 | 2/6 | 6.58 ± 1.3* | 1.0 ± 0.4* |
| RAG-2$^{-/-}$/γc$^{-/-}$ | Gd7 adult SCID liver | 0.1 | 2/6 | 0 | 0 |
| tgε26 | NP adult SCID BM | 1.0 | 3/9 | 3.8 ± 3.3* | 2.7 ± 2.1* |
| tgε26 | gd3 SCID BM | 0.6 | 3/9 | 5.9 ± 3.8* | 4.9 ± 4.8* |
| tgε26 | gd5 SCID BM | 0.5 | 3/9 | 4.7 ± 1.4* | 4.3 ± 0.8* |
| tgε26 | gd7 SCID BM | 0.4 | 3/9 | 4.9 ± 1.8* | 7.8 ± 4.3* |
| RAG-2$^{-/-}$/γc$^{-/-}$ | NP B6 MLN | 0.5 | 3/8 | 1.7 ± 1.5 | 1.2 ± 0.79 |
| RAG-2$^{-/-}$/γc$^{-/-}$ | gd3 B6 MLN | 0.6 | 1/3 | 0 | 0 |
| RAG-2$^{-/-}$/γc$^{-/-}$ | gd5 B6 MLN | 0.5 | 1/3 | 0 | 0 |
| RAG-2$^{-/-}$/γc$^{-/-}$ | gd7 B6 MLN | 0.6 | 1/3 | 0.2 ± 0.3 | 0.9 ± 0.5 |
| RAG-2$^{-/-}$/γc$^{-/-}$ | NP B6 PLN | 1.0–1.2 | 3/8 | 6.4 ± 4.6 | 14.4 ± 6.4 |
| RAG-2$^{-/-}$/γc$^{-/-}$ | gd3 B6 PLN | 1.2 | 1/3 | 15.6 ± 5.5 | 34.7 ± 10.3 |
| RAG-2$^{-/-}$/γc$^{-/-}$ | gds B6 PLN | 0.5 | 1/3 | 3.2 ± 0.8 | 2.4 ± 1.4 |
| RAG-2$^{-/-}$/γc$^{-/-}$ | gd7 B6 PLN | 1.5 | 1/3 | 14.5 ± 10.6 | 0.9 ± 0.4 |
| tgε26 | NP adult SCID SC | 0.76–1.0 | 3/9 | 2.9 ± 1.3*‡ | 1.2 ± 1.6* |
| tgε26 | gd3 SCID SC | 1.6–2.3 | 3/9 | 16.6 ± 0.4*‡§¶ | 47.4 ± 0.9*¶ |
| tgε26 | gd5 SCID SC | 2.0–2.8 | 3/9 | 21.8 ± 1.7*‡§¶ | 56.7 ± 10.9*¶ |
| tgε26 | gd7 SCID SC | 2.0–2.8 | 3/9 | 11.2 ± 5.9*‡§ | 24.4 ± 11.2* |
| RAG-2$^{-/-}$/γc$^{-/-}$ | gd3 CCR2$^{-/-}$ SC | 2.0–2.2 | 2/4 | 32.8 ± 4.7 | 57.5 ± 6.7 |
| RAG-2$^{-/-}$/γc$^{-/-}$ | gd5 CCR2$^{-/-}$ SC | 2.1–2.5 | 2/4 | 32.7 ± 11.9 | 54.4 ± 23.1 |
| RAG-2$^{-/-}$/γc$^{-/-}$ | gd3 CCR5$^{-/-}$ SC | 2.0–2.3 | 3/6 | 49.3 ± 11.0 | 70.3 ± 15.2 |
| RAG-2$^{-/-}$/γc$^{-/-}$ | gd5 CCR5$^{-/-}$ SC | 2.3–2.5 | 3/6 | 30.8 ± 6.2 | 32.6 ± 6.3* |

*significantly different from uNK$^+$ controls (p < 0.05)
‡significantly different from uNK cell densities in the MT/MLAp of the members of the same treatment group (p < 0.01)
§spleen cell recipients with significantly different uNK cell numbers than tgε26 receiving spleen cells from NP SCID donors (p < 0.001)
¶spleen cell recipients with significantly different uNK cell numbers from tgε26 receiving spleen cells from gd7 SCID donors (p < 0.01)
na—not applicable, intact thymus was transplanted Full Citations for References Referred to in the Specification 1. Stewart I J 1998 J Reprod Immunol 40:129
2. Loke Y C & King A 1995 Human Implantation. Cambridge University Press, Cambridge UK
3. Peel S 1989 Adv Anat Embryol Cell Biol 115:1
4. King, A 2000 Hum Reprod Update 6:28
5. Frey M et al 1998 J Immunol 161:400
6. Kurago Z B et al 1998 J Immunol 160:1573
7. Jokhi P P et al 1994 J Immunol 153:4427
8. Jones R K et al 1997 Biol Reprod 57:1217
9. King A & Loke Y W 1990 Cell Immunol 129:435
10. Chumbley G et al 1994 Cell Immunol 155:312
11. Hiby S E et al 1997 Mol Immunol 34:419
12. Soderstrom K et al 1997 J Immunol 159:1072
13. Zhang E G, Smith S K & Charnock-Jones D S 1999 J Soc Gynecol Invest 6, Supple 1, Abst. 158.
14. Langer N, Beach D & Lindenbaum E S, 1999 Am J Reprod Immunol 42:263
15. Croy B A et al 2000 J Soc Gynecol Invest (in revision)
16. Wang B et al 1994 PNAS 919402
17. Greenwood J D et al 2000 Placenta 20: 693–702
18. Guimond M-J, et al 1998 J Exp Med 187:217 19
19. Boehm U et al 1998 J Immunol 161:6715
20. Boehm, U et al 1997 Ann Rev Immunol 15:749
21. Delassus S et al 1994 J Immunol 152:2411
22. Platt J S & Hunt J S 1999 J Leukoc Biol 64:393
23. Saito S et al 1993 Int Immunol 5:559
24. Mossman T R & Sad S 1996 Immunol Today 17:138
25. Raghupathy R 1997 Immunol Today 18:478
26. Ashkar A A & Croy B A 1999 Biol Reprod 61:493
27. Ashkar A A & Croy, B A 2000 J Exp Med 192:259
28. De Feo V J 1967 In Cellular Biology of the Uterus. Meredith Publishing Co. New York, p 191
29. Finn C A 1996 Eur J Obstet Gynecol Reprod Biol 70:3
30. Finn C A et al 1994 J Reprod Fertil 103:153
31. Spornitz U M 1992 Adv Anat Embryol Cell Biol 124:1
32. Guimond M-J et al 1997 Biol Reprod 56:169
33. Chantakru S 1998, MSc thesis, University of Guelph
34. Chantakru S et al 1999 Placenta 20:A16
35. Clarke A G & Kendall M D 1994 Immunol Today 15:545
36. Tibbetts T A et al 1999 PNAS 96:12021
37. Ansell J D et al 1978 Clin Exp Immunol 31:397
38. Pollard J 1998 In Endocrinology of Pregnancy, FW Bazer Ed. Chapt 3, Humana Press, Boca Raton Fla.
39. Kruse A et al 1999 Biol Reprod 61:1393
40. Kruse A et al 1999 Eur J lmmunol 29:1116
41. Chantakru S et al 2000 J Reprod Immunol (in press)
42. Meekins J W et al 1994 Br J Obstet Gynaecol 101:669
43. Starzyk K A et al 1997 Hum Pathol 28:353
44. Reuvekamp A, Velsing-Aarts F V, Poulina I E et al 1999 Br J Obstet Gynecol 106:1019
45. Roberts J M et al 1989 Am J Obstet Gynecol 161:1200
46. Redman C W 1999 Am J Obstet Gynecol 180:499
47. Rinehart B K, Terrone D A, Lagoo-Deenadayalan S et al 1999 Am J
48. Feeney J G et al 1977 Lancet 1:874
49. Luppi P et al 2000 Am J Reprod Immunol 43:187
50. Robillard P Y et al 1993 J Rreprod Immunol 24:1
51. Dekker G A, Roubillard P Y & Hulsey T C 1998 Obstet Gyencol Surv 53:377
52. Li D K & Wi S. 2000 Am J Epidemiol 151:57
53. Tubbergen P, Lachmeijer A M, Althuisius S M et al 1999 J Reprod Immunol 45:81
54. Dhont M, De Sutter P, Ruyssinck et al, 1999 Am J Obstet Gynecol 181:688
55. Maman E, Lunenfeld E, Levy A et al., 1998 Fertil Steril 70:240
56. Porreco R P, Schoolcraft C L & Schoolcraft W B. 1997 J Matern Fetal Med 6:237
57. Salha O, Sharma V, Dada T et al 1999 Human Reprod 14:2268
58. Schenker J G & Ezra Y. 1994 Fertil Steril 61:411
59. Smith G N, Walker M, Tessier J L et al., 1997 Am J Obstet Gynecol 177:455
60. Tanbo T, Dale P O, Lunde O et al 1995 Obstet Gynecol 86:188
61. Yamamoto T et al 1999 Am J Reprod Immunol 41:337
62. Butcher E C et al 1999 Adv Immunol 72:209
63. Springer T A 1995 Annu Rev Physiol 57:827
64. Tedder T F et al 1995 FASEB J 9:866
65. Uksila J et al 1997 J Immunol 1581610
66. Evans S S et al 2000, Int J Hyperthermia 16:45
67. Evans S S, Schleider D M, Bowman L A et al. 1999 J Immuno 162:3615
68. Wang W C et al 1998 J Immunol 160:961
69. Hu M C-T et al 1992 Proc Natl Acad Sci 89:8254
69a. Chantakru, S., Evans, S., Wang, W. C., Croy, B. A. $6^{th}$ Annual Meeting of the Society for Natural Immunity; $18^{th}$ International Natural Killer Cell Workshop, France, May 5–9, 2000.
70. Stamper H B & Woodruff J J 1976 J Exp Med 144:828
71. Kuziel, W. A., Morgan S. J., Dawson, T. C., Giffin, S., Smithies, O., Ley, K., Maeda, N. (1997) Proc. Nat. Acad. USA 94, 12053–12058.
72. Huffnagle, G. B., McNiel, L. K., McDonald, R. A., Murphy, J. W., Toew, G. B., Kuziel, W. A. (1999) J. Immunol. 163, 4642–4646.
73. Butcher, E. C., Picker, L. J. (1996) Science 272, 60–66.
74. Kiso, Y., Yamashiro, S., McBey, B. A., Croy, B. A. (1992) Transplantation 54, 185–187.
75. Jones, R. K., Searle, R. F., Stewart, J. A., Turner, S., Bulmer, J. N., (1998) Biol. Reprod. 58, 998–1002.
76. King, A., Loke, Y. W. (1991) Immunol. Today 12, 432–435.
77. Hetherington, C. M., Humber, D. P.(1977) J. Immunogenet. 4, 271–276.
78. Koni, P. A., Sacca, R., Lawton, P., Browning, J. L., Ruddle, N. H., and Flavell, R. A. (1997) Immunity 6, 491–500.
79. Wood, G. W., Hausman, E., Choudhuri, R. (1997) Mol. Reprod. Dev. 46, 62–67.
80. Kyaw, Y., Hasegawa, G., Takatsuka, H., Shimada-Hiratsuka, M., Umezu, H., Arakawa, M, Naito, M. (1998) Arch. Histol. Cytol 61, 383–393.
81. Bany, B. M., M. B. Harvey, G. A. Schultz. 2000. J. Reprod. Fertil. 120:125.
82. Paria, B. C., J. Tan, D. B. Lubahn, S. K. Dey, and S. K. Das. 1999. Endocrinology 140:2704.
83. Finn, C. A. and L. Martin. 1972. Biol. Reprod. 7:82.
84. Sullivan, T. R. J., R. H. Karas, M. Aronovitz, G. T. Faller, J. P. Ziar, J. J. Smith, T. F. J. O'Donnell, and M. E. Mendelsohn. 1995. J. Clin. Invest. 96:2482.
85. Evans, S. S., W. C. Wang, M. D. Bain, R. Burd, J. R. Ostberg, and E. A. Repasky. 2001. Blood 97:2727.
86. Kruse, A., N. Martens, U. Fernekorn, R. Hallmann, and E. C. Butcher. 2002. Biol. Reprod. 66:333.
87. Chantakru, S., C. Miller, L. E. Roach, W. A. Kuziel, N. Maeda, W. C. Wang, S. S. Evans, and B. A. Croy. 2002. J. Immunol. 168:22.
88. PCT Application
89. Sasaki, K. and T. Ito. 1980. Arch. Histol. Jpn. 43:423.

90. Brackin, M. N., J. M. Cruse, R. E. Lewis, R. S. Hines, J. A. Stopple, and B. D. Cowan. 2002. *Exp. Mol. Pathol.* 72:91.
91. Nelson, J. D., J. J. Jato-Rodriguez, and S. Mookerjea. 1975. *Arch. Biochem. Biophys.* 169:181.
92. Tangemann, K., A. Bistrup, S. Hemmerich, and S. D. Rosen. 1999. *J. Exp. Med.* 190:935.
93. Miller, M. J., S. H. Wei, I. Parker, and M. D. Cahalan. 2002. *Science* 296:1869.
94. King, A., L. Gardner, and Y. W. Loke. 1996 *Hum. Reprod.* 11:1079.
95. Curran, E. M., L. J. Berghaus, N. J. Vernetti, A. J. Saporita, D. B. Lubahn, and D. M. Estes. 2001. *Cell Immunol.* 214:12.
96. Ogle, T. F., D. Dai, P. George, and V. B. Mahesh. 1997. *Biol. Reprod.* 57:495.
97. Jones, R. K., J. N. Bulmer, and R. F. Searle. 1995. *Hum. Reprod.* 0:3272.
98. Croy, B. A., B. A. McBey, L. A. Villeneuve, K. Kusakabe, Y. Kiso, and M. van den Heuvel. 1997. *J. Reprod. Immunol.* 32:241
99. van den Heuvel, M., B. A. McBey, A. C. Hahnel, and B. A. Croy. 1996. *J. Reprod. Immunol.* 31:37
100. Orvieto, R., Z. Ben-Rafael, A. Schwartz, R. Abir, B. Fisch, A. La-Marca, and I. Bar-Hava. 2001. *Gynecol. Endocrinol.* 15:29.
101. Ehring, G. R., H. H. Kerschbaum, C. Eder, A. L. Neben, C. M. Fanger, R. M. Khoury, P. A. Negulescu, and M. D. Cahalan. 1998. *J. Exp. Med.* 188:1593.
102. Campbell, J. J., S. Qin, D. Unutmaz, D. Soler, K. E. Murphy, M. R. Hodge, L. Wu, and E. C. Butcher. 2001. *J. Immunol.* 166:6477.
103. Robertson, M. J. 2002. *J. Leukoc. Biol.* 71:173.
104. Chantakru, S., W. A. Kuziel, N. Maeda, and B. A. Croy. 2001. *J. Reprod. Immunol.* 49:33.
105. Mazanet, M. M., K. Neote, and C. C. Hughes. 2000. *J. Immunol.* 164:5383.
106. Kansas G S et al 1993 J Exp Med 177:833.
107. Tekpetey F R, Daniel S A J & Yuzpe A 1995 J Assisted Reprod Genetics 12:720.

We claim:

1. A method of monitoring a menstrual cycle and/or pregnancy in a female comprising:
    (a) obtaining $CD56^{bright}$ natural killer cells found in blood from the female; and
    (b) contacting the $CD56^{bright}$ natural killer cells with uterine or lymphoid tissue, from a pregnant animal or an animal that has been treated with gestational hormones; and
    (c) detecting the adhesion of the $CD56^{bright}$ natural killer cells with the uterine or lymphoid tissue, wherein a greater adhesion of $CD56^{bright}$ natural killer cells from the female to the uterine or lymphoid tissue, as compared with a control indicates an immune system more competent for sustaining pregnancy.

2. The method according to claim 1, wherein the uterine tissue or lymphoid tissue is selected from sections of uterine tissue or lymphoid tissue, homogenates of uterine tissue or lymphoid tissue, adhesion molecules derived from uterine tissue or lymphoid tissue, and cells transfected with adhesion molecules derived from uterine tissue or lymphoid tissue.

3. The method according to claim 2 wherein the lymphoid or uterine tissue is selected from sections of uterine tissue or lymphoid tissue and homogenates of uterine tissue or lymphoid tissue.

4. The method according to claim 1 wherein the uterine tissue is derived from the decidua basalis.

5. The method according to claim 1 wherein the lymphoid tissue is derived from lymph node or Peyer's Patches.

6. The method according to claim 1, wherein the gestational hormone(s) comprise estrogen, progesterone, luteinizing hormone and/or chorionic gonadotropin.

7. The method according to claim 6, wherein the gestational hormone(s) comprise estrogen and/or progesterone.

8. The method according to claim 1, wherein the control is the adhesion of $CD56^{bright}$ natural killer cells found in blood from the female to uterine or lymphoid tissue from a non-pregnant animal that has not been treated with gestational hormones.

9. The method according to claim 1, wherein the control is the adhesion of $CD56^{bright}$ natural killer cells found in blood from the female to non-lymphoid or non-uterine tissue.

10. The method according to claim 9, wherein the non-lymphoid or non-uterine tissue is endothelium tissue from the pancreas.

11. The method according to claim 1 comprising:
    (a) obtaining $CD56^{bright}$ natural killer cells found in blood from the female;
    (b) contacting the $CD56^{bright}$ natural killer cells with uterine tissue from a pregnant animal; and
    (c) detecting the number and/or size of clusters of $CD56^{bright}$ natural killer cells adhered to the uterine tissue.

12. The method according to claim 11, wherein the uterine tissue is decidua basalis.

13. The method according to claim 11, wherein a greater number and/or size of clusters of $CD56^{bright}$ natural killer cells found in blood from the female adhered to the uterine tissue than with a control indicates an immune system more competent fbr sustaining pregnancy.

14. The method according to claim 13, wherein the control is the number or total size of clusters of $CD56^{bright}$ natural killer cells found in blood from a non-pregnant female adhered to the uterine tissue from a pregnant animal.

* * * * *

UNITED STATES PATENT AND TRADEMARK OFFICE
CERTIFICATE OF CORRECTION

PATENT NO.       : 7,094,561 B2                                          Page 1 of 1
APPLICATION NO.  : 10/279884
DATED            : August 22, 2006
INVENTOR(S)      : Barbara Anne Croy and Sharon S. Evans It is certified that error appears in the above-identified patent and that said Letters Patent is hereby corrected as shown below:

On the cover page, item (73) Assignees replace "University of Guelph. Niagara-on the-Lake (CN)" with --University of Guelph, Guelph, Ontario (CA)--

Signed and Sealed this

Tenth Day of March, 2009

JOHN DOLL
*Acting Director of the United States Patent and Trademark Office*